United States Patent
Huang et al.

(10) Patent No.: US 11,202,862 B2
(45) Date of Patent: Dec. 21, 2021

(54) PRESSURIZED GAS INJECTION DEVICE AND METHOD

(71) Applicant: Guo-Luen Huang, Taipei (TW)

(72) Inventors: Guo-Luen Huang, Taipei (TW); Chen-Kun Liaw, Taipei (TW)

(73) Assignee: Guo-Luen Huang, Taipei (TW)

( * ) Notice: Subject to any disclaimer, the term of this patent is extended or adjusted under 35 U.S.C. 154(b) by 215 days.

(21) Appl. No.: 16/476,862

(22) PCT Filed: Jan. 29, 2018

(86) PCT No.: PCT/CN2018/074490
§ 371 (c)(1),
(2) Date: Jul. 9, 2019

(87) PCT Pub. No.: WO2018/141234
PCT Pub. Date: Aug. 9, 2018

(65) Prior Publication Data
US 2019/0351140 A1  Nov. 21, 2019

Related U.S. Application Data

(60) Provisional application No. 62/502,878, filed on May 8, 2017, provisional application No. 62/453,884, filed on Feb. 2, 2017.

(30) Foreign Application Priority Data

Jan. 29, 2018 (WO) ................ PCT/CN2018/074490

(51) Int. Cl.
*A61M 5/20* (2006.01)
*A61M 5/32* (2006.01)

(52) U.S. Cl.
CPC ............ *A61M 5/2053* (2013.01); *A61M 5/32* (2013.01); *A61M 2005/206* (2013.01)

(58) Field of Classification Search
CPC .......... A61M 2005/006; A61M 5/2053; A61M 5/30; A61M 5/3007; A61M 5/2046;
(Continued)

(56) References Cited

U.S. PATENT DOCUMENTS

| | | | |
|---|---|---|---|
| 2002/0188249 A1 | 12/2002 | Landau | |
| 2011/0015567 A1* | 1/2011 | Azar et al. | A61M 5/30 604/70 |
| 2014/0276534 A1* | 9/2014 | Wood | A61M 5/30 604/500 |

FOREIGN PATENT DOCUMENTS

| | | |
|---|---|---|
| CN | 2680281 Y | 2/2005 |
| EP | 1474192 A2 | 11/2004 |

(Continued)

OTHER PUBLICATIONS

European Patent Office, Search Report, Patent Application Serial No. 18747925.8, dated Dec. 16, 2020, Europe.
(Continued)

*Primary Examiner* — Kami A Bosworth
*Assistant Examiner* — Emily J Becker

(57) ABSTRACT

A device and a method for adjustable quantitative injection of high-pressure gas are provided, wherein the gas may have a pressure of 5 MPa or more than 5 MPa. The gas may be directly communicated with a gas tank in the mechanism or an external gas source, flows through corresponding valves, and is charged into a predetermined or adjustable reservoir. Alternatively, the valve may be time-controllable, and does not need the reservoir. The gas is ejected through a nozzle selected based on depth or range of injection, wherein a one-way valve is disposed between the nozzle and the body to prevent contamination due to backflow. The manipulator can exert an appropriate force onto a target portion of a human for gas injection, and when the injection is done, a (Continued)

biasing member can automatically return the mechanism to its original state, ready for the next injection.

4 Claims, 22 Drawing Sheets

(58) Field of Classification Search
CPC ........ A61M 5/3015; A61M 2205/8218; A61M 2205/8225; A61M 2205/8231
See application file for complete search history.

(56) References Cited

FOREIGN PATENT DOCUMENTS

| | | |
|---|---|---|
| JP | S527189 B2 | 2/1977 |
| JP | 2015523136 A | 8/2015 |

OTHER PUBLICATIONS

Japan Patent Office, Office Action, Patent Application Serial No. 2019-562454, dated Jun. 23, 2020, Japan.

\* cited by examiner

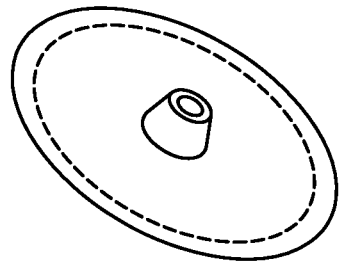
FIG. 8C
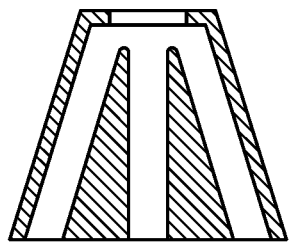
FIG. 8B
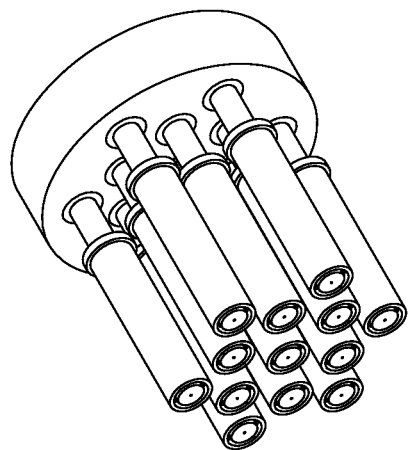
FIG. 8A
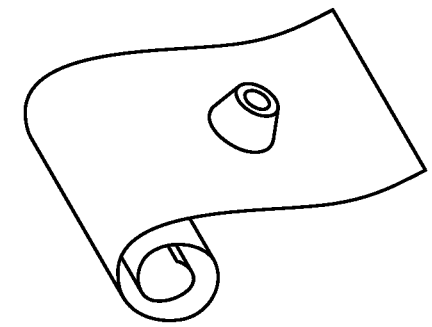
FIG. 8F
FIG. 8E
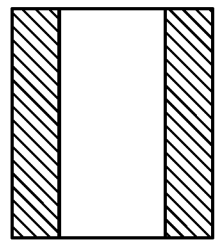
FIG. 8D

PRESSURIZED GAS INJECTION DEVICE AND METHOD

TECHNICAL FIELD

The disclosure relates to pressurized gas injection devices, and in particular to a pressurized gas injection device that injects a pressurized gas into skin without a needle.

DESCRIPTION OF THE RELATED ART

Since using needles to inject medicine usually causes patients to experience discomfort or pain, a "needle-free injection" technique has been developed. The term "needle-free injection" means that no needle is used during medicine injection. Instead, liquid medicine is squirted at a high speed in an extremely thin diameter so that the medicine penetrates the living creature's (such as a human or animal) skin and enters the body. After entering the internal tissues of a living creature, liquid medicine may diffuse along the gaps between the tissue fibers due to the characteristics of the fluid. Therefore, little damage is caused to the tissues during the entry process. Concurrently, the medicine can be effectively distributed so that absorption is facilitated However, most of the injected medicine is currently liquid. If a gas is required to serve as an injected medicine, there is often a problem wherein the molecules do not efficiently enter through the skin. Therefore, the depth and effect of the medicine injected into the target are affected. That is, with previous liquid needleless injection art, the amount of gas molecule enters deep soft tissue such as dermis, subcutaneous tissue, fascia, myofascial, muscle, or nerve tissue, is inadequate for treatment purposes, making it hard to enhance the absorption of the medicine into the human body. In addition, when a gas serves as an injected medicine, needle-free injection devices need to perform a good control of the volume of the injected gas and the injection time to ensure that requirements on efficiency and safety are taken into account.

BRIEF SUMMARY OF THE INVENTION

The purpose of the present disclosure is to provide a pressurized gas injection device and method so as to meet the requirement of high efficiency and safety.

To solve the aforementioned problems of the prior art, a pressurized gas injection device is provided in an embodiment of the present disclosure. The pressurized gas injection device includes a discharging unit, a gas storage unit, and two seal rings. The discharging unit includes a discharging opening and a vent hole. The gas storage unit is movably disposed in the discharging unit, and a gas channel is formed therein. The two seal rings are disposed on the inner wall of the discharging unit, and the seal rings abut the gas storage unit. When the gas storage unit is located at a first position relative to the discharging unit, a pressurized gas enters the gas storage unit through the vent hole and the gas channel in order, and the gas channel is located between the seal rings. In addition, when the gas storage unit moves from the first position to a second position relative to the discharging unit, the gas channel moves to be located between the seal rings and the discharging opening, and the pressurized gas in the gas storage unit is released from the pressurized gas injection device through the gas channel and the discharging opening in order, wherein the pressure of the pressurized gas is greater than or equal to 5 MPa.

Another pressurized gas injection device is provided in an embodiment of the present disclosure. The pressurized gas injection device includes a discharging unit, a first gas storage unit, a second gas storage unit, and two seal rings. The discharging unit has a discharging opening. The first gas storage unit is movably connected to the discharging unit, and a first gas injection channel and a first gas discharging channel are formed therein. The second gas storage unit is movably connected to the discharging unit, and a second gas injection channel and a second gas discharging channel are formed therein. The two seal rings are disposed on the outer surface of the discharging unit, and abut the first gas storage unit and the second gas storage unit. When the first and second gas storage units are located at a first position relative to the discharging unit, a first pressurized gas enters the first gas storage unit through the first gas injection channel, a second pressurized gas enters the second gas storage unit through the second gas injection channel, and the first and second gas discharging channels are located between the seal rings. In addition, when the first and second gas storage units move from the first position to a second position relative to the discharging unit, the first and second gas discharging channels are located between the seal rings and the discharging opening. The first pressurized gas in the first gas storage unit is released from the pressurized gas injection device through the first gas discharging channel and the discharging opening in order, and the second pressurized gas in the second gas storage unit is released from the pressurized gas injection device through the second gas discharging channel and the discharging opening in order, wherein the pressures of the first pressurized gas and the second pressurized gas are respectively greater than or equal to 5 MPa.

Another pressurized gas injection device is provided in an embodiment of the present disclosure. The pressurized gas injection device includes a discharging unit, a gas storage unit, and two seal rings. The discharging unit has a discharging opening and a temporary gas tank. The gas storage unit is movably connected to the discharging unit, and includes a sliding member and a pressurized gas tank, wherein a gas channel is formed in the sliding member, and the pressurized gas tank is detachably connected to the sliding member. The two seal rings are disposed on the inner surface of the discharging unit, and abut the gas storage unit. When the gas storage unit is located at a first position relative to the discharging unit, the gas channel is located between the seal rings, and a pressurized gas in the pressurized gas tank enters the temporary gas tank through the gas channel. In addition, when the gas storage unit moves from the first position to a second position relative to the discharging unit, a portion of the gas channel is located between the seal rings and the temporary gas tank, and the pressurized gas in the temporary gas tank is released from the pressurized gas injection device through the discharging opening, wherein the pressure of the pressurized gas is greater than or equal to 5 MPa.

Another pressurized gas injection device is provided in an embodiment of the present disclosure. The pressurized gas injection device includes a discharging unit and a major gas storage unit. The discharging unit has a discharging opening, and the major gas storage unit is communicated with the discharging unit. The major gas storage unit includes a first gas storage assembly, a first chamber, a first sliding assembly, and two first seal rings. The first gas storage assembly includes a first gas channel and the first chamber, which are communicated with each other. The first gas storage assembly is configured to contain a pressurized gas. The first sliding assembly is movably disposed around the outside of the first gas storage assembly. The two first seal rings are disposed on the inner wall of the first sliding assembly, and are located between the first sliding assembly and the first gas storage assembly. When the first sliding assembly is located at a first closed position relative to the first gas storage assembly, a portion of the first gas channel is located between the first seal rings and the discharging unit to avoid the pressurized gas in the first chamber entering the discharging unit through the first gas channel. In addition, when the first sliding assembly moves from the first closed position to a first open position relative to the first gas storage assembly, the first gas channel is located between the first seal rings. The pressurized gas in the first chamber enters the discharging unit through the first gas channel, and is released from the pressurized gas injection device through the discharging opening, wherein the pressure of the pressurized gas is greater than or equal to 5 MPa.

Another pressurized gas injection device is provided in an embodiment of the present disclosure. The pressurized gas injection device includes a discharging unit, a gas storage unit, a biasing assembly, a first seal ring, and a second seal ring. The discharging unit has a discharging opening and a protruding portion. The gas storage unit includes a hollow core tube and a gap adjusting component. The core tube is disposed in the discharging unit, and is slidable relative to the discharging unit, wherein the protruding portion extends into the core tube, and the core tube has a vent hole corresponding to the discharging opening. The gap adjusting component is movably disposed in the core tube, and the gap adjusting component has a gas channel. The biasing assembly is disposed between the discharging unit and the core tube. The first seal ring is disposed on the protruding portion, and abuts the core tube. The second seal ring is disposed on the gap adjusting component, and abuts the core tube, wherein an exit of the gas channel is towards the core tube, and is located between the first seal ring and the second seal ring. When the core tube is located at a first position relative to the discharging unit, the first seal ring is located between the vent hole and the exit to avoid a pressurized gas entering the vent hole from the gas channel. When an elastic force is exerted by the biasing assembly to drive the core tube to move from the first position to a second position relative to the discharging unit, the vent hole is located between the first seal ring and the second seal ring. In addition, the pressurized gas enters the gas adjusting component from an entrance of the gas channel, and the pressurized gas is released from the pressurized gas injection device through the vent hole and the discharging opening in order, wherein the pressure of the pressurized gas is greater than or equal to 5 MPa.

A method for injecting a pressurized gas is provided in an embodiment of the present disclosure. The method includes providing a discharging unit, providing a gas storage unit communicated with the discharging unit and configured to store the pressurized gas, providing a core tube, which has a vent hole, movably connected to the discharging unit and the gas storage unit, and providing a biasing assembly, wherein the biasing assembly pushes the core tube to move relative to the discharging unit and the gas storage unit, the vent hole is communicated with the gas storage unit and the discharging unit in a specific period to release the pressurized gas in the gas storage unit through the vent hole and the discharging unit in order, and the pressurized gas is injected into a human body.

The advantage of the present disclosure is that the gas storage unit is movable relative to the discharging unit and forces the pressurized gas to pass through skin and reach subcutaneous tissues, so that good therapeutic results can be achieved. On the other hand, it is also possible to appropriately increase or decrease the number of auxiliary gas storage units and control them in the closed or open position, thereby selectively providing different volumes of pressurized gas, and thereby enabling quantitative volume control of the injected gas.

BRIEF DESCRIPTION OF THE DRAWINGS

FIGS. 8A-8F are perspective views illustrating nozzles of the pressurized gas injection device in accordance with different embodiments of the present disclosure.

Figure 1A:
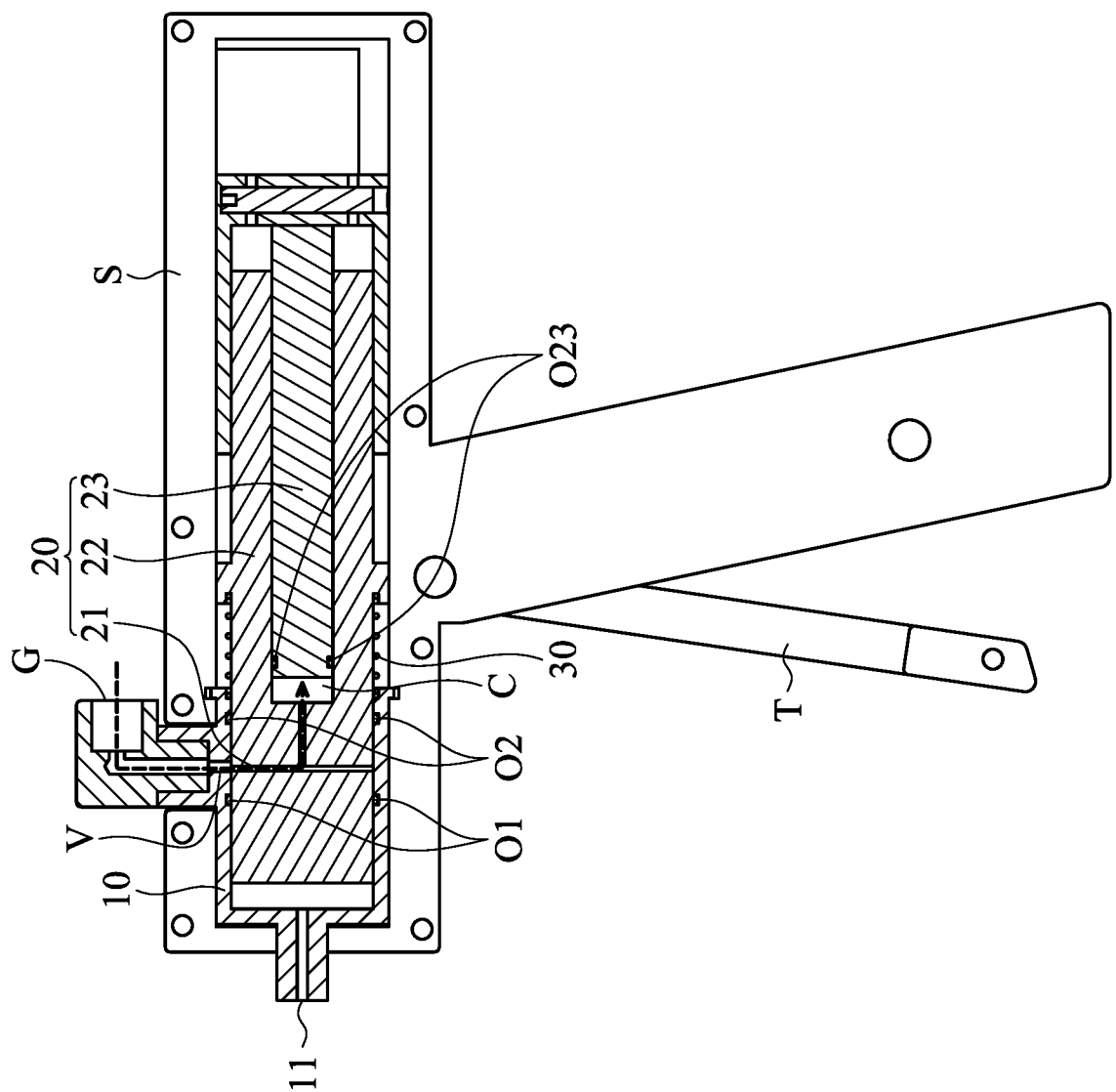
FIG. 1A is a cross-sectional view illustrating a pressurized gas injection device in accordance with an embodiment of the present disclosure, wherein a gas storage unit is located at a first position relative to a discharging unit.

Numerals shown in the drawings are listed as follows:
1~pressurized gas injection device
10~discharging unit
11~discharging opening
12~temporary gas tank
13~protruding portion
20~gas storage unit
20A~first gas storage unit
20B~second gas storage unit
20'~auxiliary gas storage unit
21~gas channel
21I~first inlet gas channel
21I'~second gas injection channel
21O~first gas discharging channel
21O'~second gas discharging channel
22~body
23~rod
24~sliding member
25~pressurized gas tank
26~first gas storage assembly
27~first sliding assembly
26'~second gas storage assembly
27'~second sliding assembly
28~gap adjusting component
29~core tube
30~biasing assembly
40~one-way valve
41~bullet-shaped gas tank
C, C', C1, C2~chamber
E~exit
G~gas injection opening
H~housing
H1~first gas injection opening
H2~second gas injection opening
I~entrance
N~pin
O1, O1', O2, O2', O3, O4, O23~seal ring
P~nozzles
Q~socket
S~casing
T~driving mechanism
U~gas source
U1, U2~pipeline
V~vent hole

DETAILED DESCRIPTION OF THE INVENTION

Embodiments of the present disclosure are described herein in accompany with the appended figures.

First, referring to FIG. 1A, a pressurized gas injection device 1 includes a casing S and a driving mechanism T (such as a movable trigger) in an embodiment of the present disclosure. A discharging unit 10, a gas storage unit 20, and at least two seal rings O1 and O2 are disposed in the casing S. The discharging unit 10 has a discharging opening 11 and a vent hole V, and the discharging opening 11 is configured to release a pressurized gas from the pressurized gas injection device 1. The gas storage unit 20 is movably disposed in the discharging unit 10, and the gas storage unit 20 includes a hollow body 22 and a rod 23. The rod 23 is plugged in the body 22 with an adjustable position, and a chamber C is formed between the body 22 and the rod 23. The chamber C is configured to store the pressurized gas. In addition, a gas channel 21 is formed in the body 22, and the gas channel 21 is communicated with the chamber C. The two seal rings O1 and O2 are disposed on the inner wall of the discharging unit 10, and abut the body 22. The seal rings O1 and O2 are configured to avoid the gas leaking.

In this embodiment, the pressure of the pressurized gas, which is injected into the chamber C, may be greater than or equal to 5 MPa. It should be noted that, in this embodiment, the rod 23 may move forward or backward in the body 22 by rotating through the corresponding thread structures (not shown) located on the rod 23 and the body 22. Therefore, the volume of the chamber C may be changed to achieve the purpose of providing and adjusting different quantitative volumes for gas injection, wherein a seal ring O23 is disposed between the rod 23 and the inner wall of the body 22.

Still referring to FIG. 1A, the driving mechanism T is pivotally connected to the casing S and the gas storage unit 20. The driving mechanism T may be pressed by an external force to rotate relative to the casing S, and thereby the gas storage unit 20 is driven to move in the discharging unit 10. Before the driving mechanism T is pressed, the gas storage unit 20 is located at a first position (FIG. 1A) relative to the discharging unit 10. At this time, the opening of the gas channel 21 is located between the two seal rings O1 and O2, and is directly communicated with the vent hole V. Therefore, a pressurized gas may enter the chamber C of the gas storage unit 20 (shown as the arrow direction in FIG. 1A) through a gas injection opening G, the vent hole V and the gas channel 21 in order, wherein the gas injection opening G is located on the casing S, and the vent hole V is communicated with the gas injection opening G. Therefore, the pressurized gas injection device 1 is in a charged state.

Figure 1B:
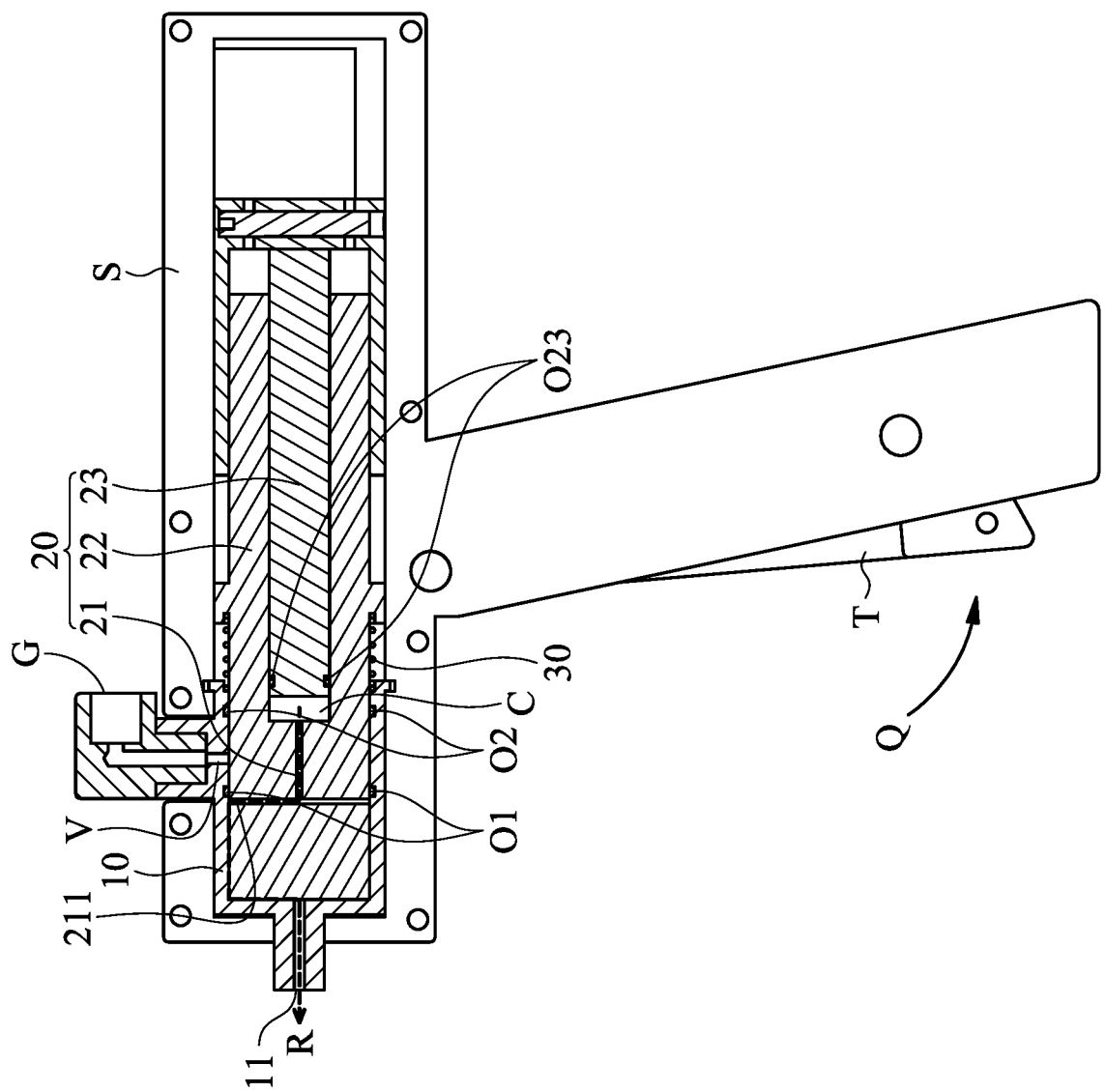
FIG. 1B is a cross-sectional view illustrating that the gas storage unit moves to a second position relative to the discharging unit.
Figure 1C:
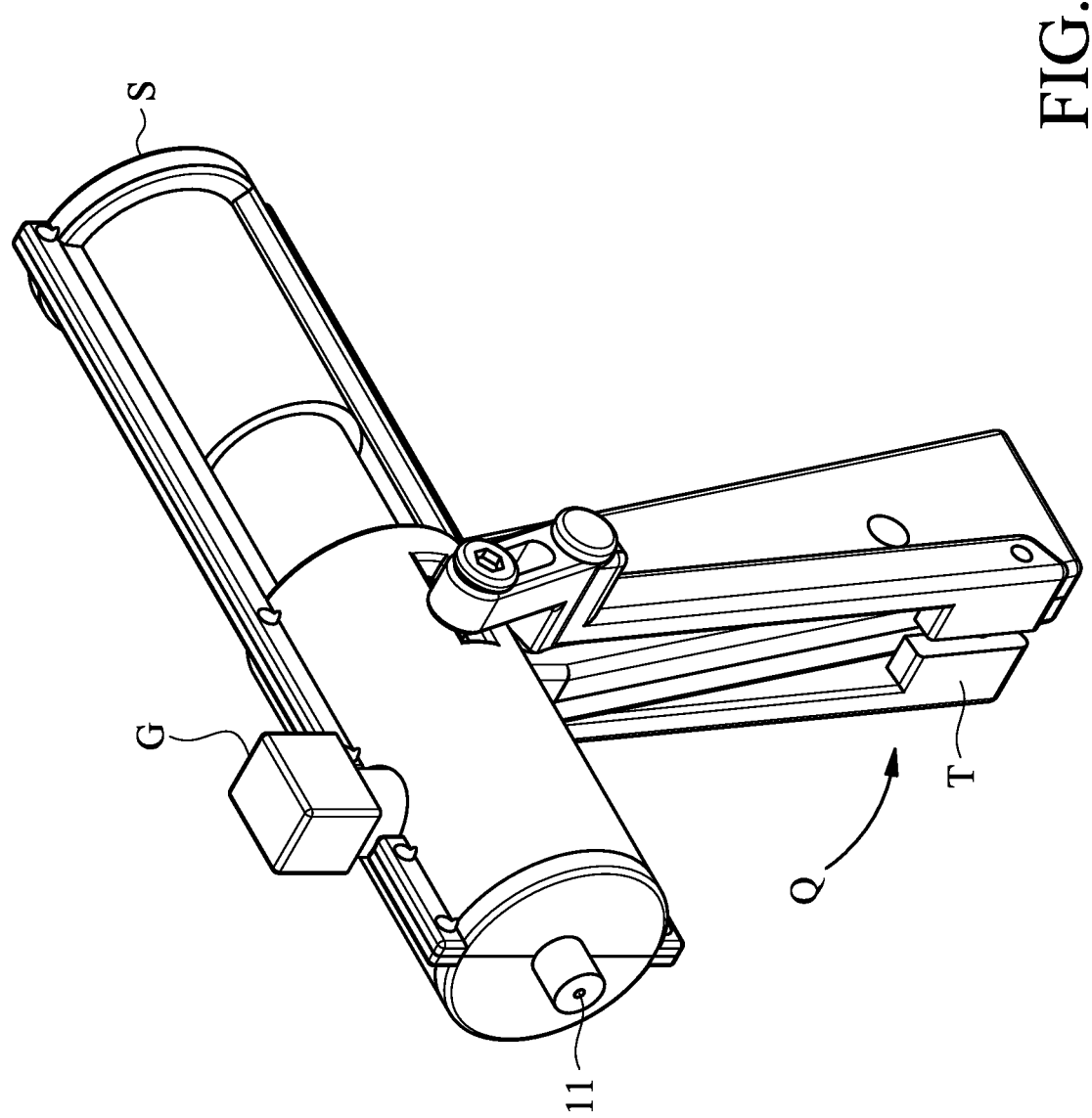
FIG. 1C is a perspective view illustrating the pressurized gas injection device when the gas storage unit moves to the second position relative to the discharging unit.

Then, referring to FIGS. 1B and 1C, FIG. 1B shows a cross-sectional view illustrating that the gas storage unit 20 moves from the first position to a second position relative to the discharging unit 10. When users press the driving mechanism T, the gas storage unit 20 may move from the first position to the second position relative to the discharging unit 10. At this time, since the opening 21I of the gas channel 21 moves to be located between the discharging opening 11 and the two seal rings O1 and O2, the pressurized gas in the chamber C may be released from the pressurized gas injection device 1 (shown as the arrow direction in FIG.

1B) through the gas channel 21 and the discharging opening 11 in order. Therefore, the pressurized gas injection device 1 is in an exhausted state.

Next, when users release the driving mechanism T, a biasing assembly 30 (such as a compressed spring) disposed between the gas storage unit 20 and the discharging unit 10 may provide an elastic force such that the gas storage unit 20 is driven to return from the second position (FIG. 1B) to the first position shown in FIG. 1A relative to the discharging unit 10. The pressurized gas, with a pressure greater than or equal to 5 MPa, may directly penetrate the skin and reach dermis or deeper subcutaneous place through the aforementioned mechanical design. Therefore, good healing effect can be achieved.

Figure 2A:
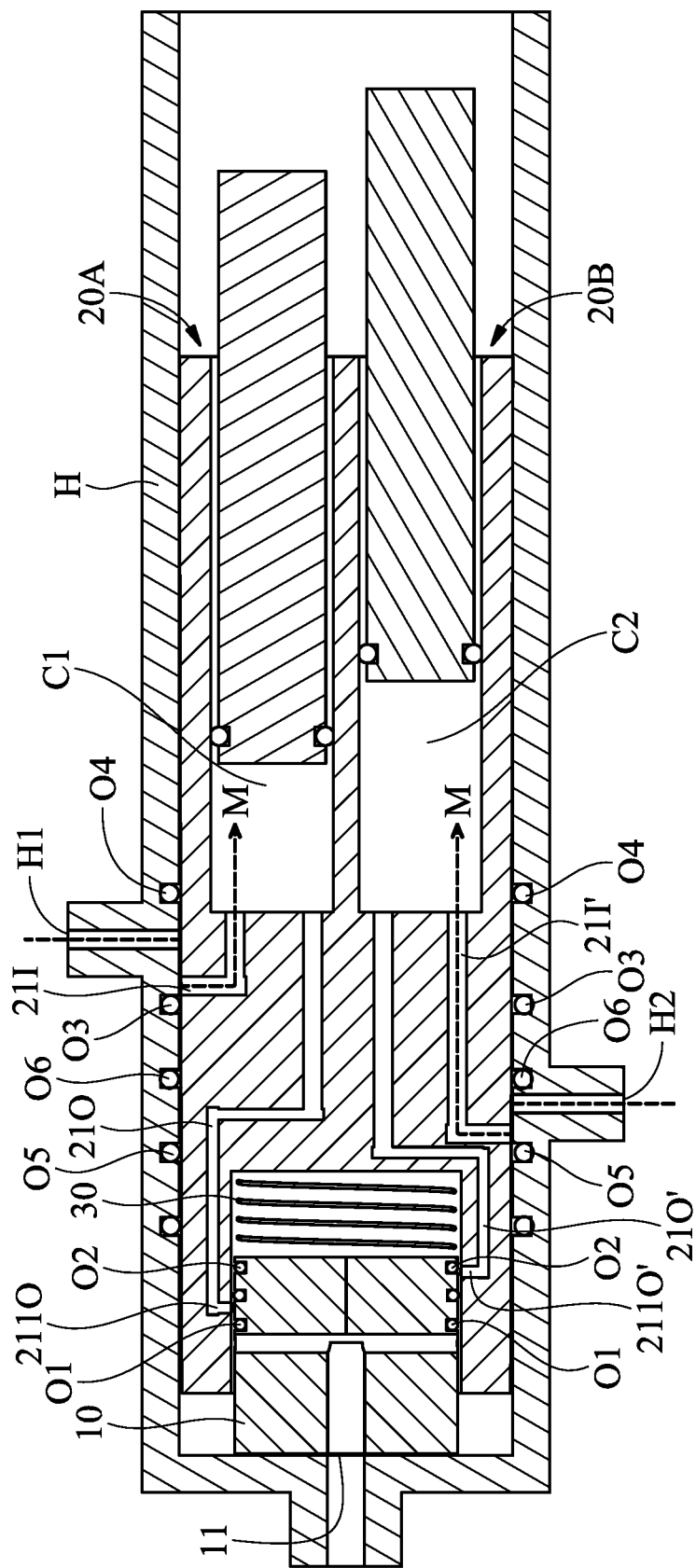
FIG. 2A is a cross-sectional view illustrating the pressurized gas injection device in accordance with another embodiment of the present disclosure, wherein a first gas storage unit and a second gas storage unit are located at the first position relative to the discharging unit.

Next, referring to FIG. 2A, the main difference between the pressurized gas injection device 1 in another embodiment of the present disclosure and the pressurized gas injection device 1 shown in FIGS. 1A and 1B is that, in this embodiment, the pressurized gas injection device 1 further includes a set of gas storage units (including a first gas storage unit 20A and a second gas storage unit 20B), which are located side by side, and fixed with each other. In addition, a housing H is further disposed outside the discharging unit 10, the first gas storage unit 20A, and the second gas storage unit 20B. As shown in FIG. 2A, the discharging unit 10 has the discharging opening 11, wherein a first gas injection channel 21I and a first gas discharging channel 21O are formed in the upper first gas storage unit 20A, and a second gas injection channel 21I' and a second gas discharging channel 21O' are formed in the lower second gas storage unit 20B. The two seal rings O1 and O2 are disposed on the outer surface of the discharging unit 10, and the seal rings O1 and O2 abut the inner sidewalls of the first gas storage unit 20A and the second gas storage unit 20B. Therefore, the gas is avoided leaking from the gap between the discharging unit 10 and the gas storage units 20A and 20B.

Still referring to FIG. 2A, the pressurized gas injection device 1 further includes two first injection seal rings O3 and O4, two second injection seal rings O5 and O6, and a biasing assembly 30. The housing H has a first gas injection opening H1 and a second gas injection opening H2, which are provided for respectively injecting a gas into a chamber C1 of the first gas storage unit 20A and a chamber C2 of the second gas storage unit 20B (shown as the arrow direction M in FIG. 2A). It should be appreciated that the two first injection seal rings O3 and O4 are disposed on the inner wall of the housing H, and correspond to the first gas injection opening H1 to avoid the gas leaking. The two second injection seal rings O5 and O6 are disposed on the inner wall of the housing H, and correspond to the second gas injection opening H2 to avoid the gas leaking. In addition, the biasing assembly 30 (such as a compressed spring) is disposed between the discharging unit 10 and the two gas storage units 20A and 20B.

It should be noted that when the biasing assembly 30 is in an initial state (as shown in FIG. 2A), the first gas storage units 20A and the second gas storage unit 20B are located at a first position relative to the discharging unit 10. Also, the first gas injection channel 21I is located between the two first gas injection seal rings O3 and O4, and the second gas injection channel 21I' is located between the two second gas injection seal rings O5 and O6. That way, shown as the arrow direction M in FIG. 2A, a first pressurized gas may enter the chamber C1 of the first gas storage unit 20A through the first gas injection opening H1 and the first gas injection channel 21I in order. A second pressurized gas may enter the chamber C2 of the second gas storage unit 20B through the second gas injection opening H2 and the second gas injection channel 21I' in order.

Since the first gas discharging channel 21O and the second gas discharging channel 21O' are respectively located between the two seal rings O1 and O2, at this time, the gas is blocked and unable to be released from the pressurized gas injection device 1 through the discharging opening 11. Therefore, the pressurized gas injection device 1 is in a charged state, wherein the first pressurized gas entering the chamber C1 through the first gas injection opening H1 is not mixed with the second pressurized gas entering the chamber C2 through the second gas injection opening H2. In this embodiment, each of the pressures of the first pressurized gas and the second pressurized gas may be greater than or equal to 5 MPa, and the pressure values of the first pressurized gas and the second pressurized gas may be different.

Figure 2B:
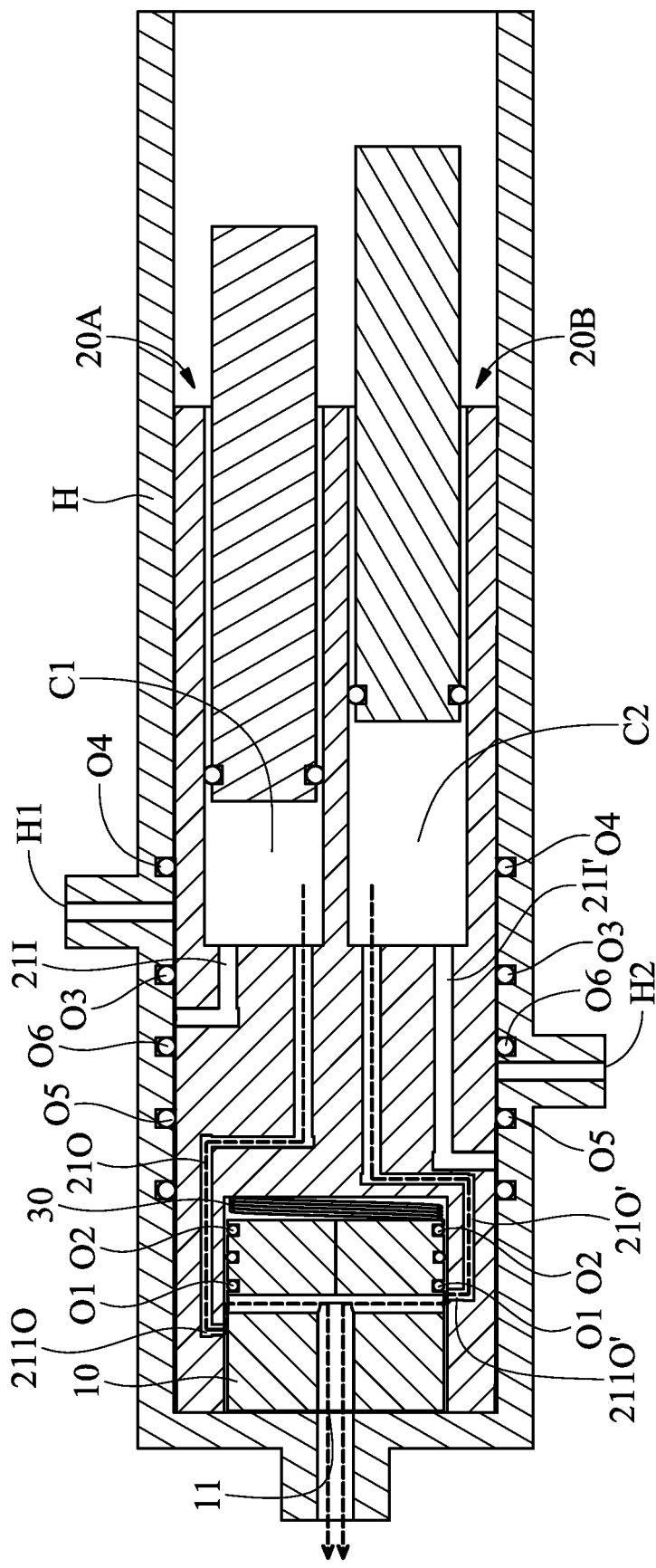
FIG. 2B is a cross-sectional view illustrating that the first gas storage unit and the second gas storage unit move to the second position relative to the discharging unit.

Then, referring to FIG. 2B, FIG. 2B is a cross-sectional view illustrating that the first gas storage unit 20A and the second gas storage unit 20B move from the first position to the second position relative to the discharging unit 10. As shown in FIG. 2B, when the pressurized gas needs to be released to perform an injection, an external force may be applied through a trigger or another driving mechanism, and thereby the first gas storage unit 20A and the second gas storage unit 20B are driven to move from the first position towards the discharging opening 11 to the second position relative to the discharging unit 10. That way, the biasing assembly 30 is further compressed. In this state, the first gas discharging channel 21O and the second gas discharging channel 21O' would move to be located between the two seal rings O1, O2, and the discharging opening 11. Therefore, the first pressurized gas in the first gas storage unit 20A may be released from the pressurized gas injection device 1 through the first gas discharging channel 21O and the discharging opening 11 in order. Similarly, the second pressurized gas in the second gas storage unit 20B may also be released from the pressurized gas injection device 1 through the second gas discharging channel 21O' and the discharging opening 11 in order. Thus, the pressurized gas injection device 1 is in an exhausted state.

The pressurized gas, with a pressure greater than or equal to 5 MPa, may directly penetrate the skin and reach dermis or deeper subcutaneous place through the aforementioned mechanical design. Therefore, good healing effect can be achieved. On the other hand, different chambers C1 and C2 may be used by the first gas storage unit 20A and the second gas storage unit 20B to respectively store the first pressurized gas and the second pressurized gas. Therefore, different gases may be mixed together to serve as an injected medicine.

Figure 3A:
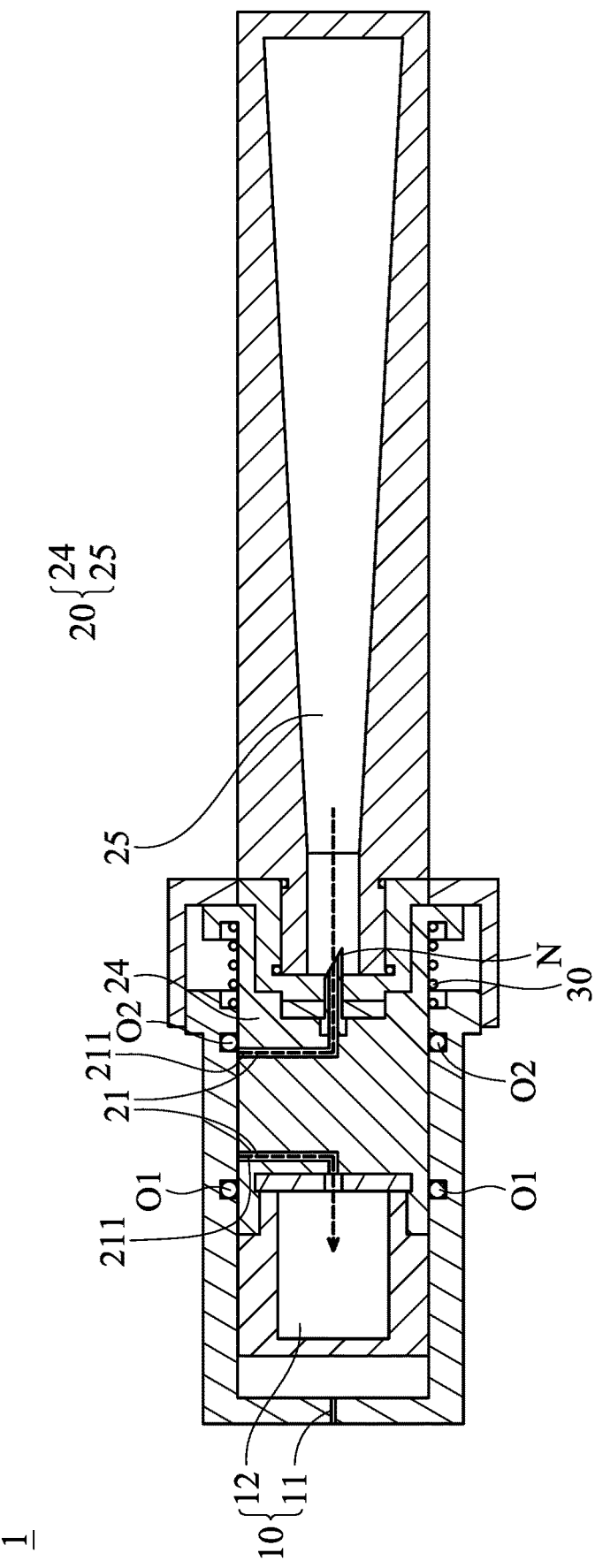
FIG. 3A is a cross-sectional view illustrating the pressurized gas injection device in accordance with another embodiment of the present disclosure, wherein the gas storage unit is located at the first position relative to the discharging unit.

Referring to FIG. 3A, the pressurized gas injection device 1 in another embodiment of the present disclosure mainly includes a discharging unit 10, a gas storage unit 20, two seal rings O1 and O2, a biasing assembly 30, and a pin N. As shown in FIG. 3A, the discharging unit 10 has a discharging opening 11 and a temporary gas tank 12. The temporary gas tank 12 is detachable and replaceable to change the size of the inner volume for achieving the purpose of adjusting and providing injected gases with different quantitative volumes. The gas storage unit 20 is movably connected to the discharging unit 10, and the gas storage unit 20 includes a sliding member 24 and a pressurized gas tank 25. It should be noted that the pressurized gas tank 25 is detachably connected to the sliding member 24, and a gas channel 21 is formed in the sliding member 24. The two seal rings O1 and O2 are disposed on the inner wall of the discharging unit 10, and abut the outer surface of the gas storage unit 20 to avoid the gas leaking. The pin N is disposed on one side of the sliding member 24, and is configured to pierce a seal (not shown), which is made of a metal or plastic material, on the pressurized gas tank 25. Therefore, the pressurized gas may enter the gas channel 21 from the pressurized gas tank 25.

Still referring to FIG. 3A, when the gas storage unit 20 is at a first position relative to the discharging unit 10, the openings 211 of the gas channel 21 is located between the two seal rings O1 and O2. Accordingly, the pressurized gas in the pressurized gas tank 25 would pass through the gas channel 21 and enter the temporary gas tank 12 so that the pressurized gas injection device 1 is in a charged state. In this embodiment, the pressure of the pressurized gas may be greater than or equal to 5 MPa.

Figure 3B:
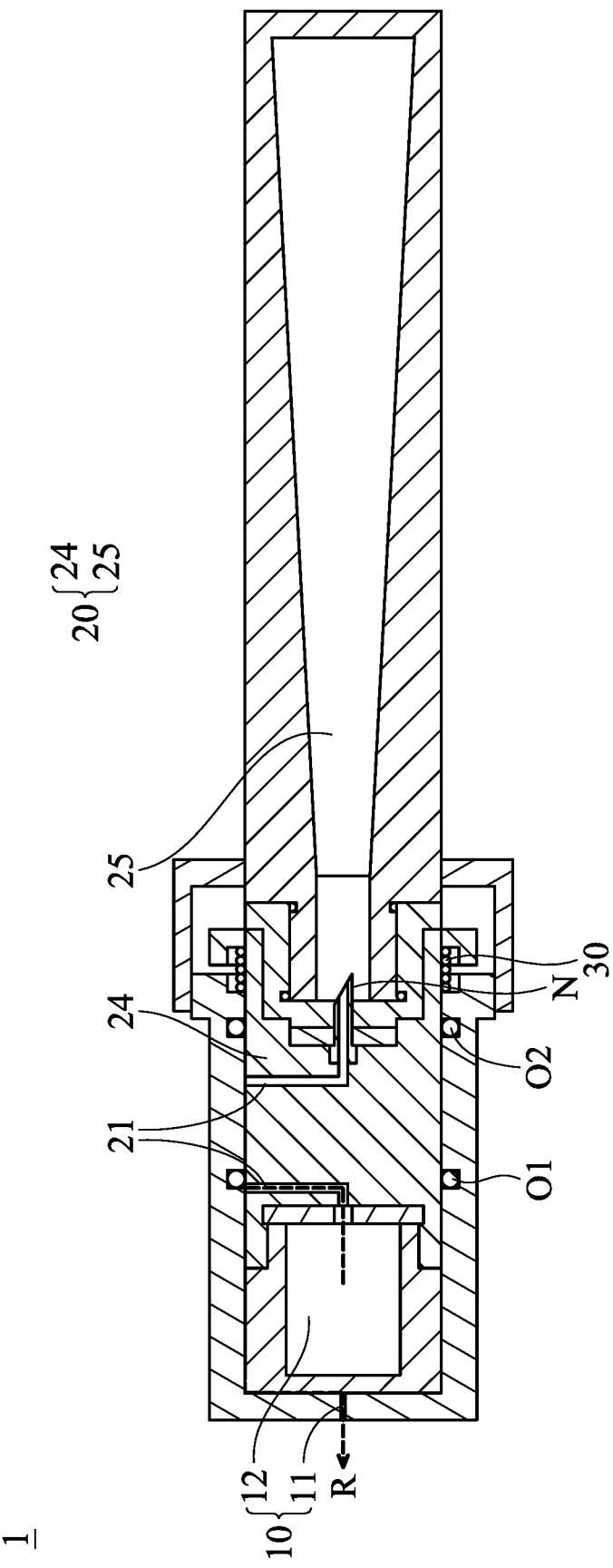
FIG. 3B is a cross-sectional view illustrating that the gas storage unit moves to the second position relative to the discharging unit.

Next, referring to FIG. 3B, FIG. 3B is a cross-sectional view illustrating that the gas storage unit 20 in FIG. 3A moves from the first position to the second position relative to the discharging unit 10. As shown in FIG. 3B, when the pressurized gas needs to be released to perform an injection, an external force may be applied to the pressurized gas tank 25 to push the gas storage unit 20 to move from the first position to the second position relative to the discharging unit 10. At this time, since the opening 211 of the gas channel 21 near the temporary gas tank 12 is not located between the two seal rings O1 and O2, and is located between the two seal rings O1 and O2 and the temporary gas tank 12, instead. Therefore, the pressurized gas in the temporary gas tank 12 may be released from the pressurized gas injection device 1 (shown as the arrow direction R in FIG. 3B) through the discharging opening 11. Thus, the pressurized gas injection device 1 is in an exhausted state.

The pressurized gas, with a pressure greater than or equal to 5 MPa, can directly penetrate the skin and reach dermis or deeper subcutaneous place through the aforementioned mechanical design. Therefore, good healing effect can be achieved. On the other hand, the pressurized gas injection device 1 not is only convenient for carrying, but patients may also be able to change and inject the pressurized gas themselves by arranging the detachable pressurized gas tank 25. Therefore, the convenience for treatment can be enhanced.

Figure 3C:
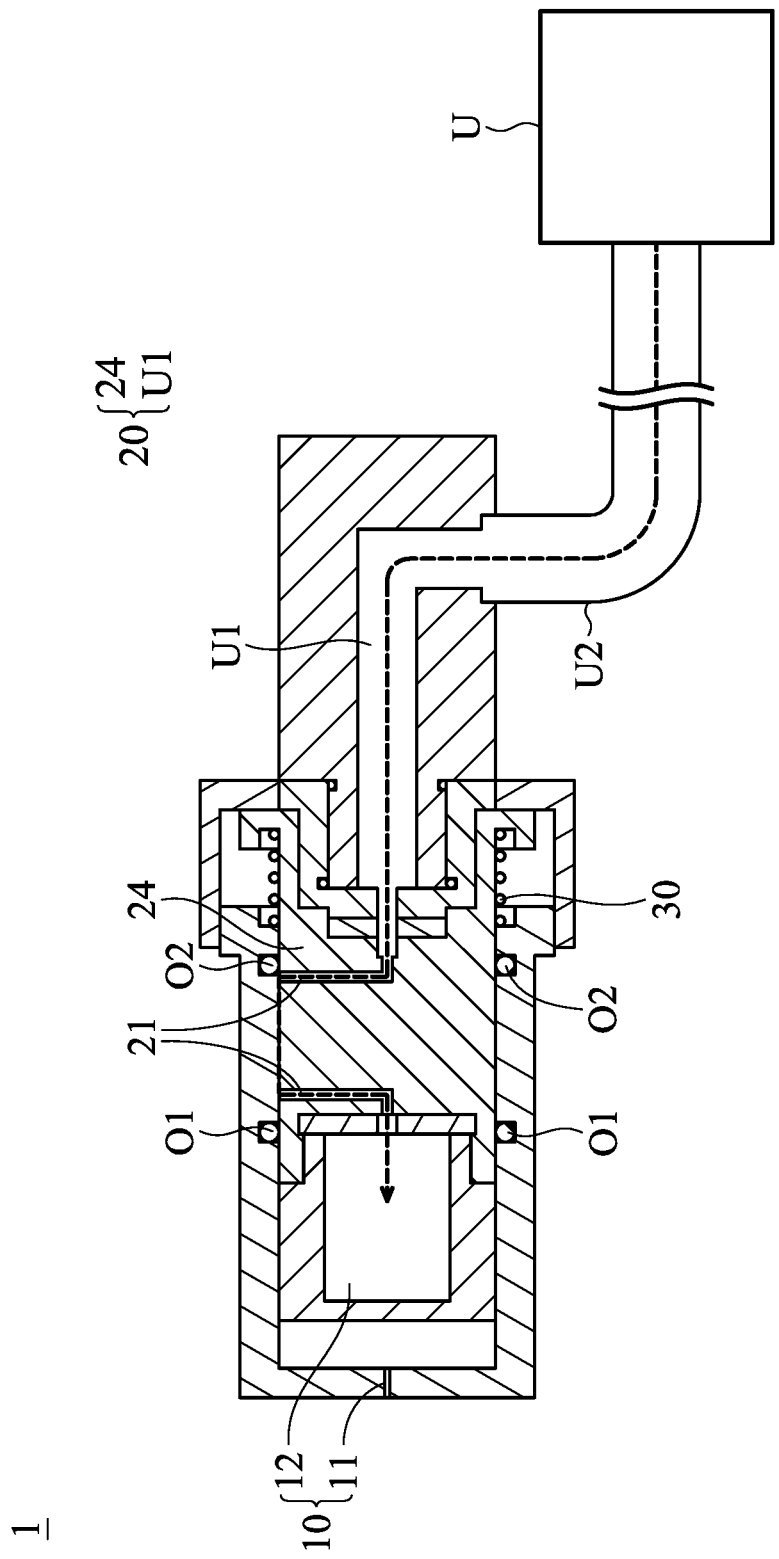
FIG. 3C is a cross-sectional view illustrating that the pressurized gas injection device is communicated with an external gas source.

In addition, as shown in FIG. 3C, in another embodiment, the detachable pressurized gas tank 25 may not be used. Instead, the gas channel 21 in the sliding member 24 is communicated with an external large gas source U through pipelines U1 and U2. Therefore, the pressurized gas is continuously provided into the pressurized gas injection device 1, wherein the sliding member 24 and the pipeline U1 may constitute the gas storage unit 20.

Figure 4A:
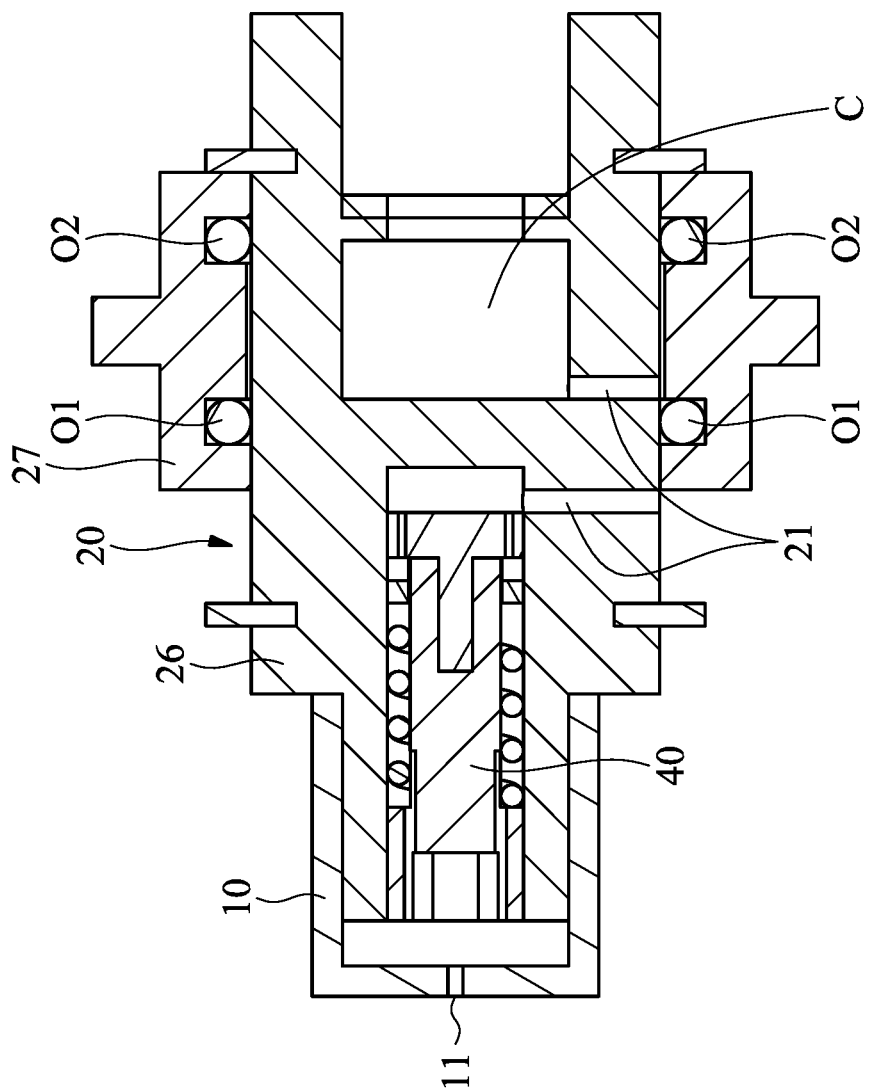
FIG. 4A is a cross-sectional view illustrating the pressurized gas injection device in accordance with another embodiment of the present disclosure, wherein a first sliding assembly is located at a first closed position relative to a first gas storage assembly.

Referring to FIG. 4A, in another embodiment of the present disclosure, the pressurized gas injection device 1 includes a discharging unit 10, a major gas storage unit 20, and a one-way valve 40. The discharging unit 10 has a discharging opening 11, and the major gas storage unit 20 is communicated with the discharging unit 10 through the one-way valve 40, wherein the major gas storage unit 20 includes a first gas storage assembly 26, a first sliding assembly 27, and two first seal rings O1 and O2. A first gas channel 21 and a first chamber C are formed in the first gas storage assembly 26, wherein the first chamber C may be configured to contain a pressurized gas, and the first sliding assembly 27 is movably disposed around the outside of the first gas storage assembly 26. In addition, the two first seal rings O1 and O2 are disposed on the inner wall of the first sliding assembly 27, and abut the outer surface of the first gas storage assembly 26 to avoid the gas leaking.

Still referring to FIG. 4A, when the first sliding assembly 27 is located at a first closed position relative to the first gas storage assembly 26, the first gas channel 21 is closed because a portion of the first gas channel 21 near the discharging unit 10 is located between the two first seal rings O1, O2, and the discharging unit 10. Therefore, the pressurized gas in the first chamber C may be prevented from entering the discharging unit 10 through the first channel 21 and the one-way valve 40, and the pressurized gas injection device 1 may be in a charged state. In this embodiment, the pressure of the pressurized gas may be greater than or equal to 5 MPa. It should be noted that the discharging unit 10 may also be communicated with multiple gas storage unit in series to achieve the purpose of adjusting and providing different quantitative volumes of the injected gas. The detailed structure may be referred to the description in the following embodiments.

Figure 4B:
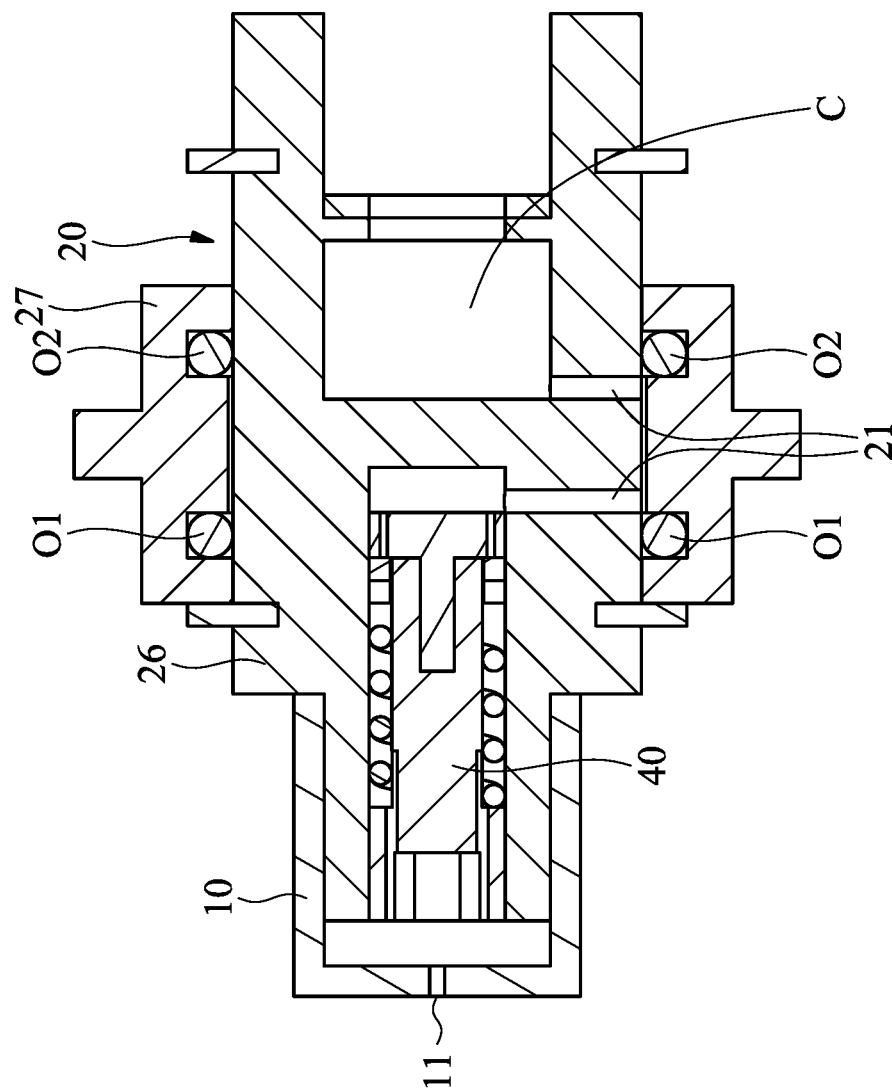
FIG. 4B is a cross-sectional view illustrating that the first sliding assembly is located at a first open position relative to the first gas storage assembly.

Next, referring to FIG. 4B, FIG. 4B is a cross-sectional view illustrating that the first sliding assembly 27 moves from the first closed position to a first open position relative to the first gas storage assembly 26. As shown in FIG. 4B, when the pressurized gas needs to be released to perform an injection, the first sliding assembly 27 may move to the first open position relative to the first gas storage assembly 26. Also, the first gas channel 21 is located between the two first seal rings O1 and O2. At this time, the pressurized gas in the first chamber C may enter the discharging unit 10 through the first gas channel 21 and the one-way valve 40, and the pressurized gas is released from the pressurized gas injection device 1 through the discharging opening 11. Meanwhile, the pressurized gas injection device 1 is in an exhausted state. The pressurized gas, with a pressure greater than or equal to 5 MPa, may directly penetrate the skin and reach dermis or deeper subcutaneous place through the aforementioned mechanical design. Therefore, good healing effect can be achieved.

Figure 4C:
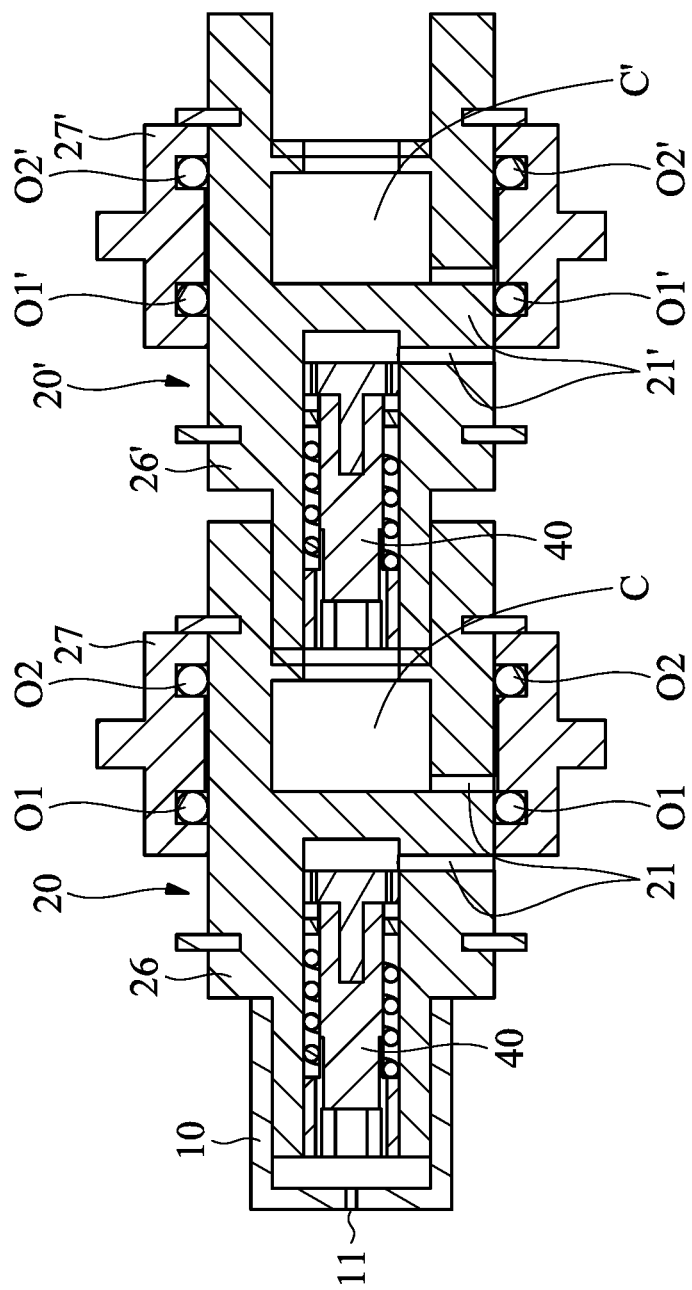
FIG. 4C is a cross-sectional view illustrating the pressurized gas injection device in accordance with another embodiment of the present disclosure, wherein a second sliding assembly is located at a second closed position relative to a second gas storage assembly.

Then, referring to FIG. 4C, in another embodiment of the present disclosure, the pressurized gas injection device 1 includes the discharging unit 10, the major gas storage unit 20, and the one-way valve 40, and further includes an auxiliary gas storage unit 20' and another one-way valve 40. The auxiliary gas storage unit 20' may be communicated with the major gas storage unit 20 through the one-way valve 40. As shown in FIG. 4C, the auxiliary gas storage unit 20' includes a second gas storage assembly 26', a second sliding assembly 27', and two second seal rings O1' and O2', wherein a second gas channel 21' and a second chamber C' are formed in the second gas storage assembly 26'. The second chamber C' may be configured to contain the pressurized gas. In this embodiment, the second sliding assembly 27' is movably disposed around the outside of the second gas storage assembly 26'. The two second seal rings O1' and O2' are disposed on the inner wall of the second sliding assembly 27', and abut the outer surface of the second gas storage assembly 26' to avoid the gas leaking.

Still referring to FIG. 4C, when the second sliding assembly 27' is located at a second closed position relative to the second gas storage assembly 26', the second gas channel 21' is closed because a portion of the second gas channel 21' near the major gas storage unit 20 is located between the two second seal rings O1', O2', and the major gas storage unit 20. Therefore, the pressurized gas in the second chamber C' may be prevented from entering the major gas storage unit 20 through the second gas channel 21' and the one-way valve 40.

Figure 4D:
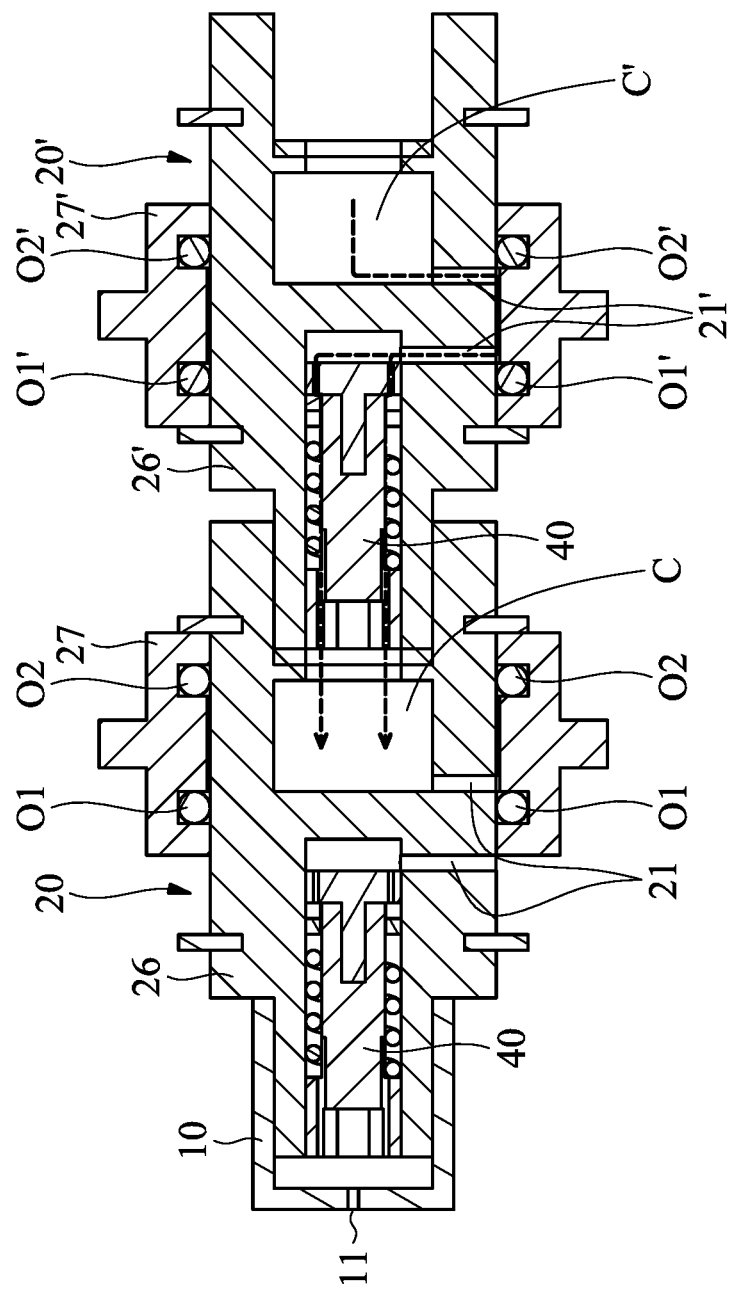
FIG. 4D is a cross-sectional view illustrating that the second sliding assembly moves to a second open position relative to the second gas storage assembly.

Next, referring to FIG. 4D, FIG. 4D is a cross-sectional view illustrating that the second sliding assembly 27' moves from the second closed position to a second open position relative to the second gas storage assembly 26'. As shown in FIG. 4D, when the second sliding assembly 27' moves to the second open position relative to the second gas storage assembly 26', the second gas channel 21' will be located between the two second seal rings O1' and O2'. Accordingly, the pressurized gas in the second chamber C' may enter the major gas storage unit 20 through the second channel 21' and the one-way valve 40. Therefore, the pressurized gas injection device 1 is in a charged state. Similarly, when the pressurized gas needs to be released to perform an injection, the first sliding assembly 27 may move to the first open position (as shown in FIG. 4B) relative to the first gas storage assembly 26 so that the pressurized gas in the first chamber C may enter the discharging unit 10 through the first gas channel 21 and the one-way valve 40. Thus, the pressurized gas is released from the pressurized gas injection device 1 through the discharging opening 11. In this embodiment, the pressure of the pressurized gas is greater than or equal to 5 MPa.

Figure 4E:
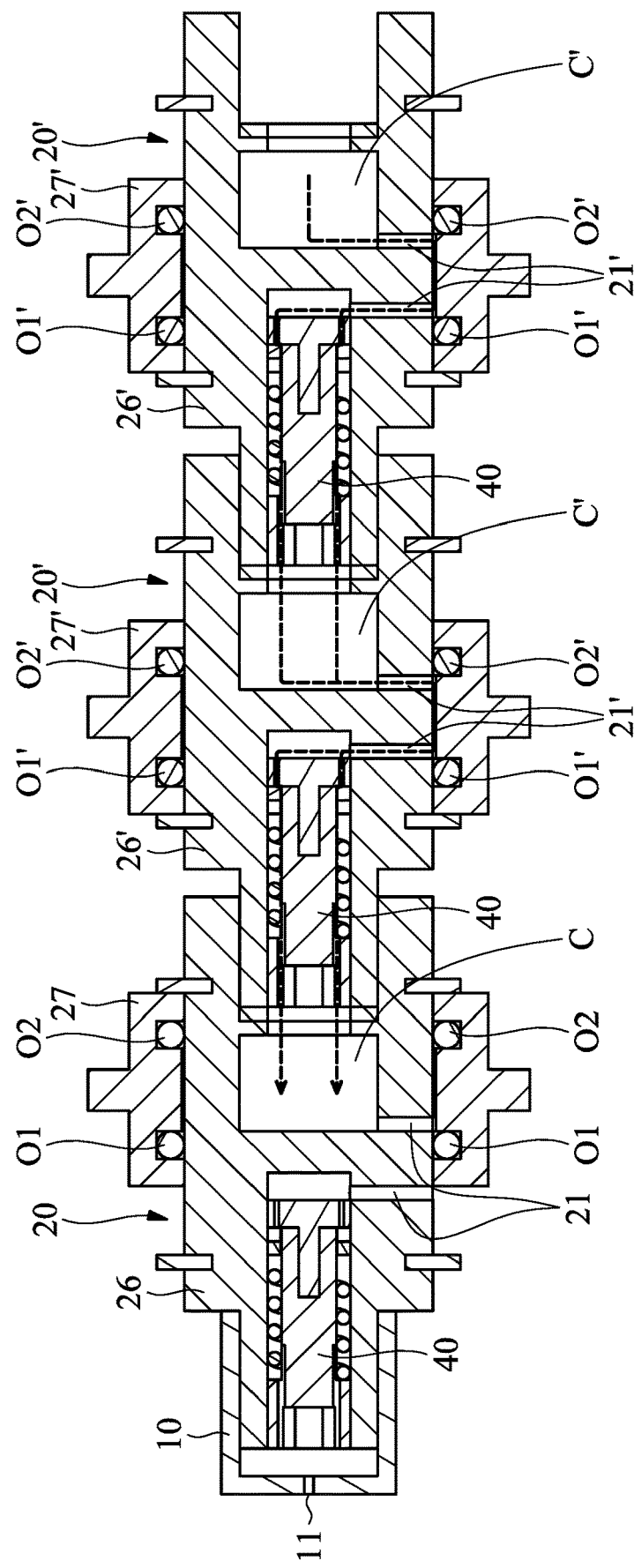
FIG. 4E is a cross-sectional view illustrating the pressurized gas injection device in accordance with another embodiment of the present disclosure, wherein the pressurized gas injection device includes two auxiliary gas storage units.

Referring to FIG. 4E, the main difference between this embodiment and the embodiment shown in FIG. 4D is that the pressurized gas injection device 1 further includes two auxiliary gas storage units 20' communicated with each other through the one-way valve 40. As shown in FIG. 4E, when both the second sliding assemblys 27' of the two auxiliary gas storage units 20' are located at the second open position relative the second gas storage assembly 26', the pressurized gas injection device 1 is in a charged state. In addition, the total volume of the pressurized gas contained in the pressurized gas injection device 1 in FIG. 4E may be greater than that in the pressurized gas injection device 1 in FIG. 4D. In other words, in this embodiment, the pressurized gases with different volumes may be selectively provided for injection by increasing or adjusting the quantity of the auxiliary gas storage units 20', and switching the second sliding assembly 27' between the closed or open positions.

Figure 5A:
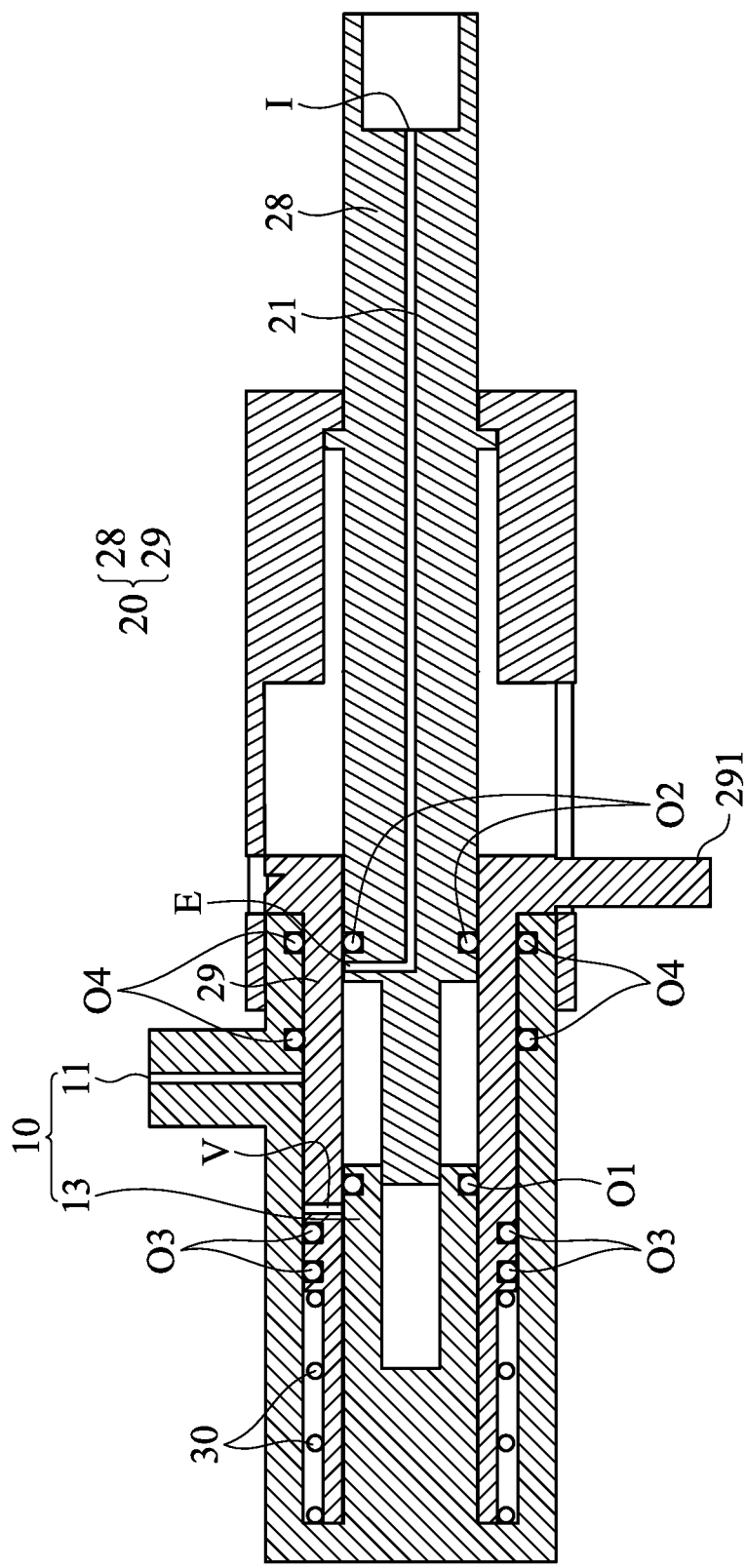
FIG. 5A is a cross-sectional view illustrating the pressurized gas injection device in accordance with another embodiment of the present disclosure, wherein a core tube of the gas storage unit is located at the first position relative to the discharging unit.

Then, referring to FIG. 5A, in another embodiment of the present disclosure, the pressurized gas injection device 1 includes a discharging unit 10, a gas storage unit 20, a biasing assembly 30, a first seal ring O1, a second seal ring O2, two third seal rings O3, and two fourth seal rings O4. The discharging unit 10 has a discharging opening 11 and a protruding portion 13. The gas storage unit 20 includes a gap adjusting component 28 and a hollow core tube 29. As shown in FIG. 5A, the core tube 29 is disposed in the discharging unit 10, and may slide relative to the discharging unit 10, wherein the protruding portion 13 extends into the core tube 29, and the core tube 29 has a vent hole V corresponding to the discharging opening 11.

It should be noted that the gap adjusting component 28 is movably disposed in the core tube 29, and a gas channel 21 is formed in the gap adjusting component 28. The biasing assembly 30 is disposed between the discharging unit 10 and the core tube 29. The first seal ring O1 is disposed around the protruding portion 13, and abuts the core tube 29. The second seal ring O2 is disposed on the gap adjusting component 28, and abuts the core tube 29. In addition, an exit E of the gas channel 21 faces the core tube 29, and is located between the first seal ring O1 and the second seal ring O2. The two third seal rings O3 are disposed on the core tube 29, abut the discharging unit 10, and are located between the biasing assembly 30 and the vent hole V. On the other hand, the two fourth seal rings O4 are disposed on the discharging unit 10, and abut the outer surface of the core tube 29. The discharging opening 11 is located between the two third seal rings O3 and the two fourth seal rings O4.

Still referring to FIG. 5A, when an external force is applied to the biasing assembly 30 (for example, a push rod 291 at the bottom of the core tube 29 is pressed by a hand), and the biasing assembly 30 is in a compressed state, the core tube 29 is located at a first position relative to the discharging unit 10. At this time, the first seal ring O1 is located between the vent hole V and the exit E, and the vent hole V is located between the first seal ring O1 and the two third seal rings O3. Therefore, the gas channel 21 can be prevented from communicating with the vent hole V to avoid the pressurized gas in the gas channel 21 leaking through the vent hole V, and the pressurized gas injection device 1 is in a charged state. In this embodiment, the pressure of the pressurized gas may be greater than or equal to 5 MPa.

Figure 5B:
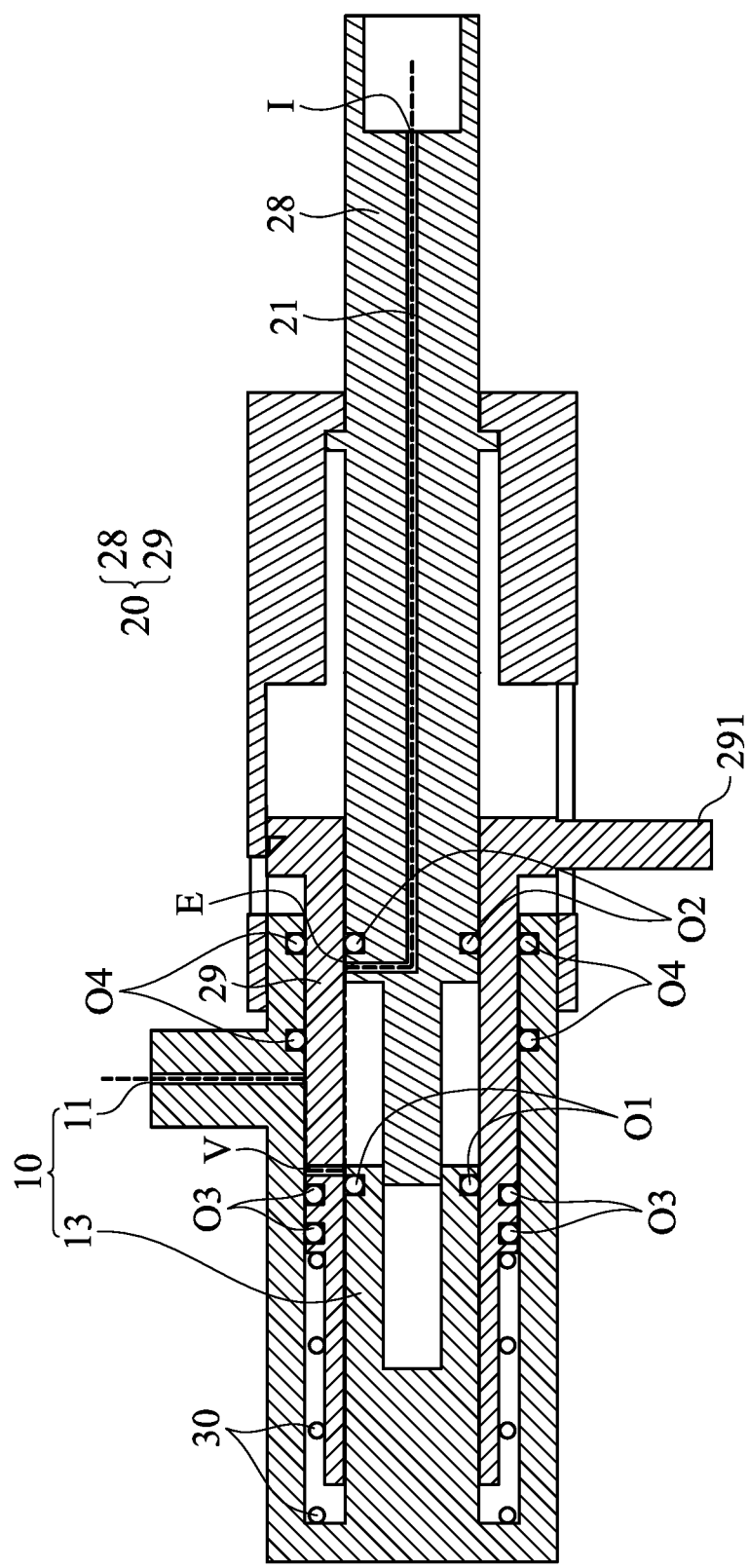
FIG. 5B is a cross-sectional view illustrating that the core tube of the gas storage unit moves to the second position relative to the discharging unit.

Next, referring to FIG. 5B, FIG. 5B is a cross-sectional schematic view illustrating that the core tube 29 moves from the first position to the second position relative to the discharging unit 10. As shown in FIG. 5B, after the external force applied to the push rod 291 at the bottom of the core tube 29 is released, the biasing assembly 30 (such as a compressed spring) may return to a released state by its elastic force, and the elastic force may drive the core tube 29 to move from the first position to the second position relative to the discharging unit 10. It should be noted that, at this time, the position of the vent hole V is between the first seal ring O1 and the second seal ring O2, and the position of the vent hole V is concurrently between the two third seal rings O3 and the two fourth seal rings O4. Therefore, the pressurized gas injected from the entrance I into the gas channel 21 may pass through the gap adjusting component 28 and the exit E, and reach the vent hole V. Sequentially, the pressurized gas may further be released from the pressurized gas injection device 1 through the vent hole V and the discharging opening 11 in order so that the pressurized gas is in an exhausted state. The pressurized gas, with a pressure greater than or equal to 5 MPa, may directly penetrate the skin and reach dermis or deeper subcutaneous place through the aforementioned mechanical design. Therefore, good healing effect can be achieved.

Figure 5C:
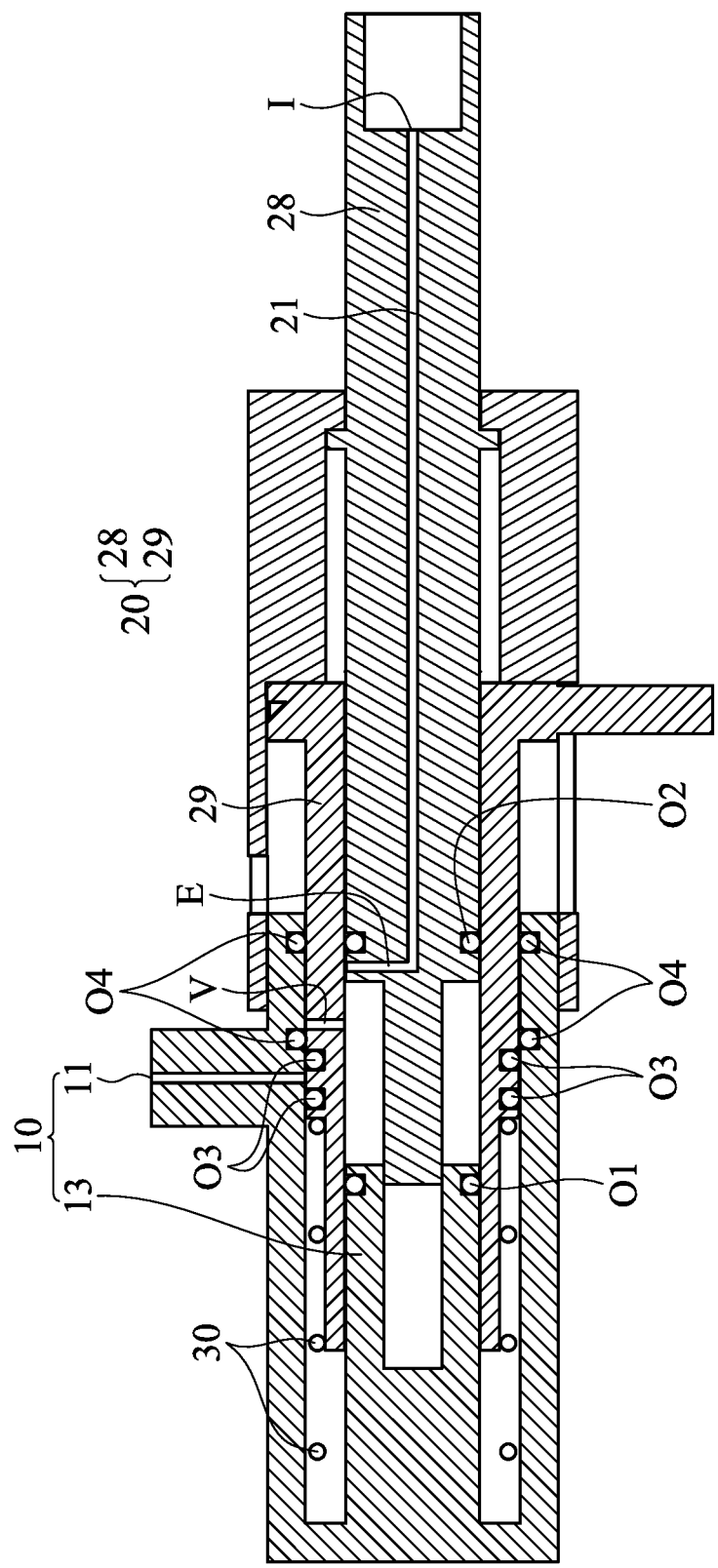
FIG. 5C is a cross-sectional view illustrating that the core tube of the gas storage unit moves to a third position relative to the discharging unit.

Referring to FIG. 5C, FIG. 5C is a cross-sectional schematic view illustrating that the core tube 29 further moves to a third position relative to the discharging unit 10. As shown in FIG. 5C, when the biasing assembly 30 further drives the core tube 29 to slide from the second position to the third position relative to the discharging unit 10 through the elastic force, the position of one of the third seal rings O3/the fourth seal rings O4 is between the vent hole V and the discharging opening 11. Accordingly, the pressurized gas in the vent hole V may be prevented from flowing towards the discharging opening 11. It is shown in FIGS. 5A, 5B, and 5C that the second position (FIG. 5B) is between the first position (FIG. 5A) and the third position (FIG. 5C). When the core tube 29 slides to the third position, the exhausted state of the pressurized gas injection device 1 ends. Until the push rod 291 is pushed back and compresses the biasing assembly 30, the core tube 29 returns to the state shown in FIG. 5A relative to the discharging unit 10, facilitating to charge the pressurized gas injection device 1 again. In this embodiment, because the multistage flow control may be performed by arranging the biasing assembly and different seal rings, the effect of high pressure and constant quantity injection can be achieved. Thus, the flexibility and convenience in use can be enhanced.

Figure 6A:
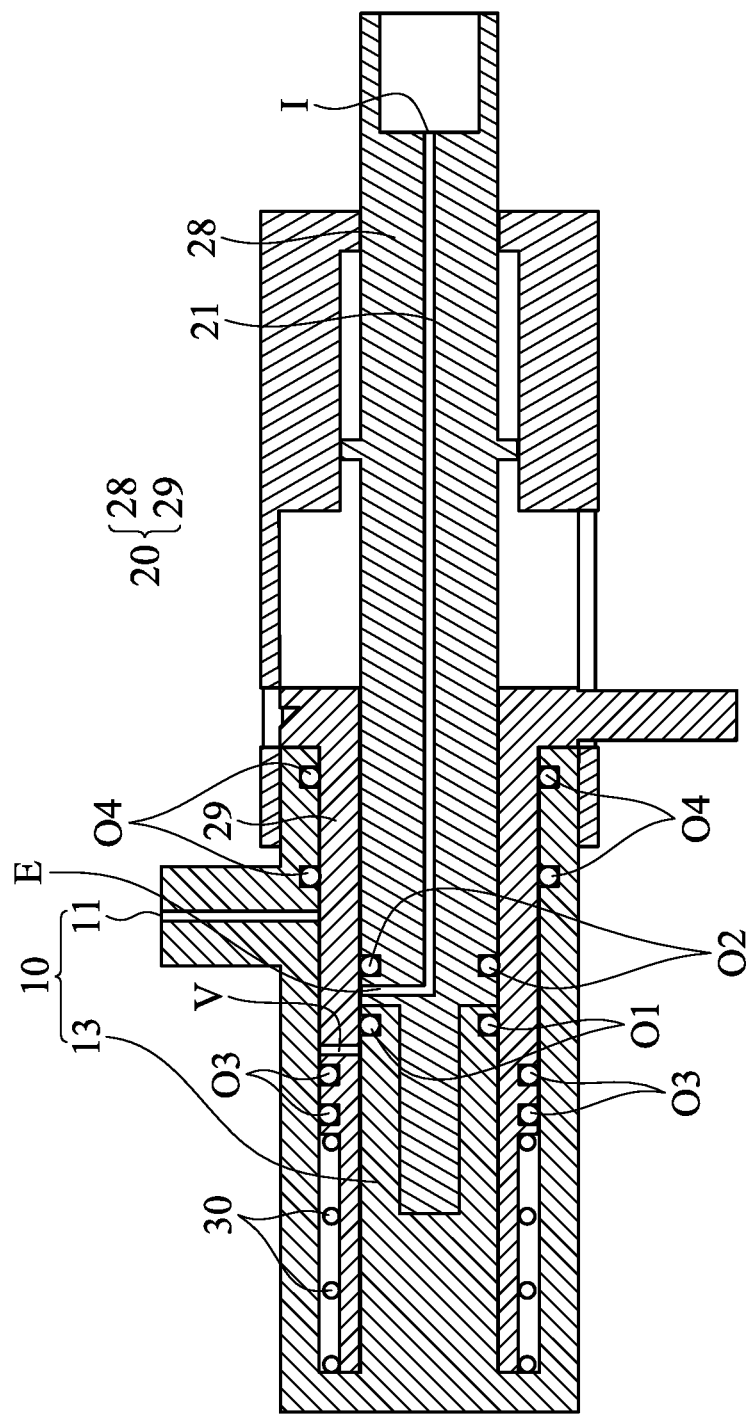
FIG. 6A is a cross-sectional view illustrating that a minimum gap is adjusted between a gap adjustment component and a protruding portion, and the core tube of the gas storage unit is located at the first position relative to the discharging unit.

Then, referring to FIG. 6A, FIG. 6A is a cross-sectional view illustrating that the core tube 29 of the gas storage unit 20 is located at the first position relative to the discharging unit 10, the gap adjustment component 28 rotates to enter the discharging unit 10 through the thread structure (not shown), and a minimum gap is between the gap adjustment component 28 and the protruding portion 13. As shown in FIG. 6A, when the biasing assembly 30 is in a compressed state, the core tube 29 is located at the first position relative to the discharging unit 10. Meanwhile, the first seal ring O1 is located between the vent hole V and the exit E of the gas channel 21, and thereby the pressurized gas may be avoided entering the vent hole V from the gas channel 21.

Figure 6B:
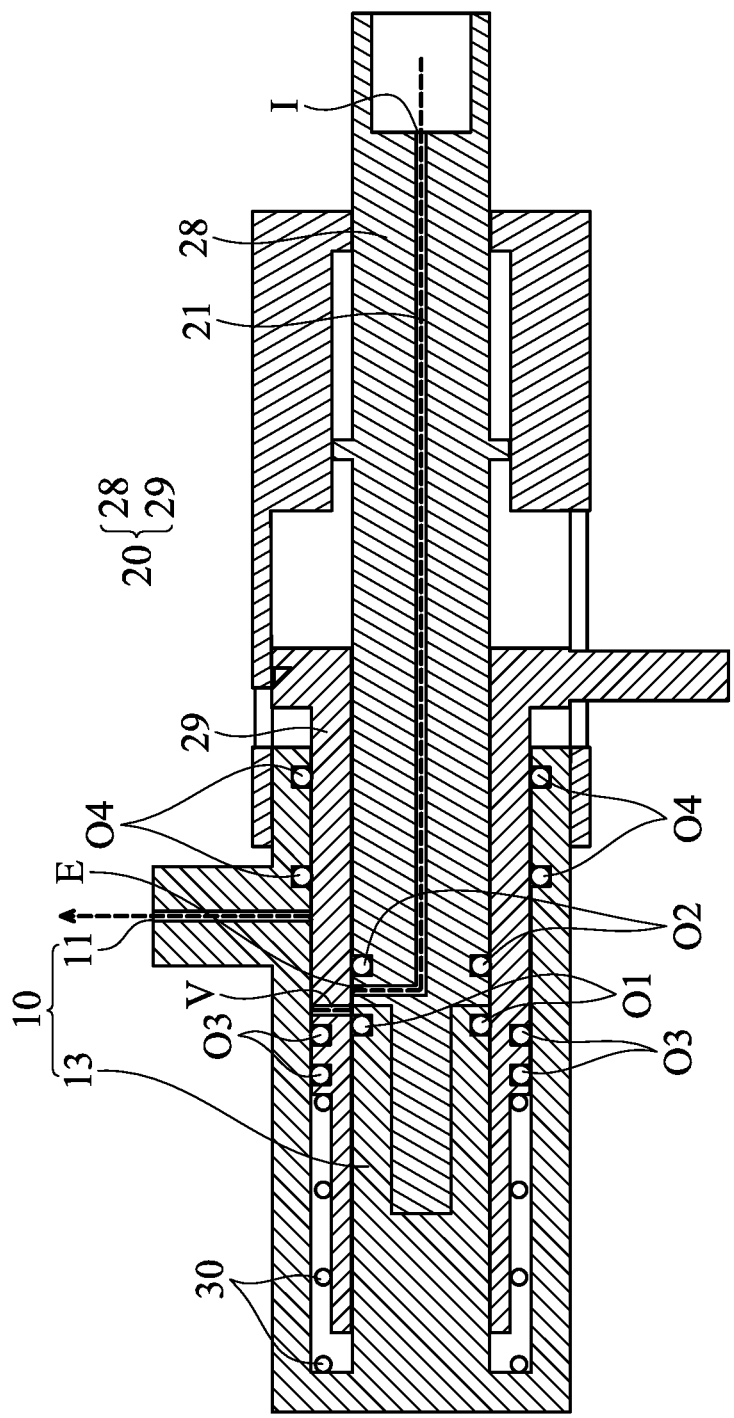
FIG. 6B is a cross-sectional view illustrating that the core tube of the gas storage unit moves to the second position relative to the discharging unit.

Referring to FIG. 6B, FIG. 6B is a cross-sectional view illustrating that the core tube 29 in FIG. 6A moves from the first position to the second position relative to the discharging unit 10. As shown in FIG. 6B, the biasing assembly 30 is in a released state, and the core tube 29 is driven to move to the second position relative to the discharging unit 10 by the elastic force. Since the vent hole V is between the first seal ring O1 and the second seal ring O2, and the position of the vent hole V is also between the two third seal rings O3 and the two fourth seal rings O4, the pressurized gas may inject from the entrance I of the gas channel 21 into the gap adjusting component 28. The pressurized gas is released from the pressurized gas injection device 1 through and the vent hole V and the discharging opening 11 in order. Therefore, the pressurized gas injection device 1 is in an exhausted state.

Figure 6C:
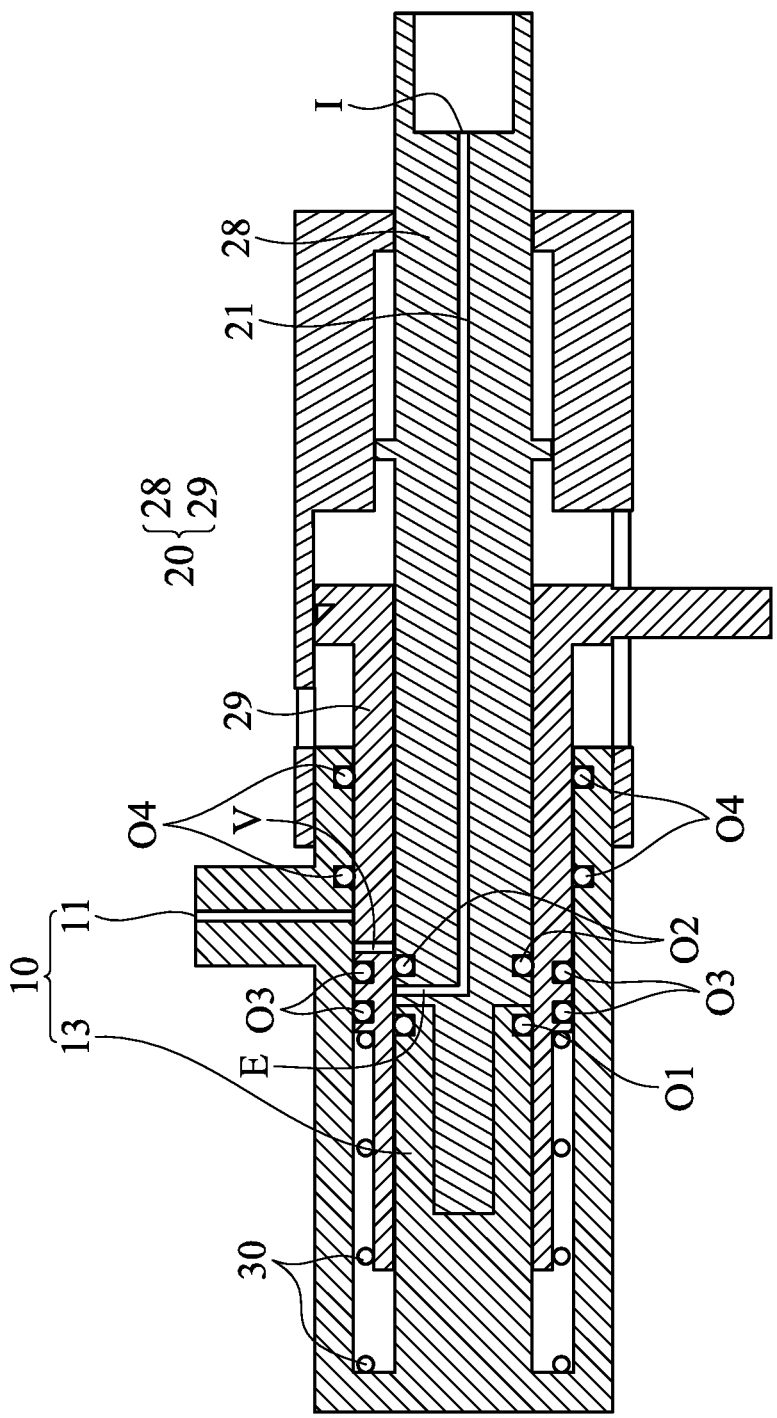
FIG. 6C is a cross-sectional view illustrating that the core tube of the gas storage unit moves to a fourth position relative to the discharging unit.

Next, referring to FIG. 6C, FIG. 6C is a cross-sectional view illustrating that the core tube 29 in FIG. 6A continuously moves to a fourth position relative to the discharging unit 10 by releasing the biasing assembly 30. As shown in FIG. 6C, the gap between the gap adjusting component 28 and the protruding portion 13 has been adjusted to a minimum gap. Therefore, the distance between the first seal ring O1 and the second seal ring O2 is also shortened. Accordingly, in the process that the biasing assembly 30 further drives the core tube 29 to slide from the second position to the fourth position relative to the discharging unit 10, the vent hole V may be just shortly located between the second seal ring O2 and the fourth seal rings O4. Therefore, the required time communicating the vent hole V with the gas channel can be reduced to avoid the pressurized gas in the gas channel 21 excessively flowing out of the discharging opening 11. That is, at this time, the pressurized gas injection device 1 is in a discharging ending state. As set forth above, in this embodiment, the time releasing the pressurized gas is selectively set by adjusting the gap between the gap adjusting component 28 and the protruding portion 13. That way, a good control direct to the discharging amount and the injection time of the gas can be performed.

Figure 6D:
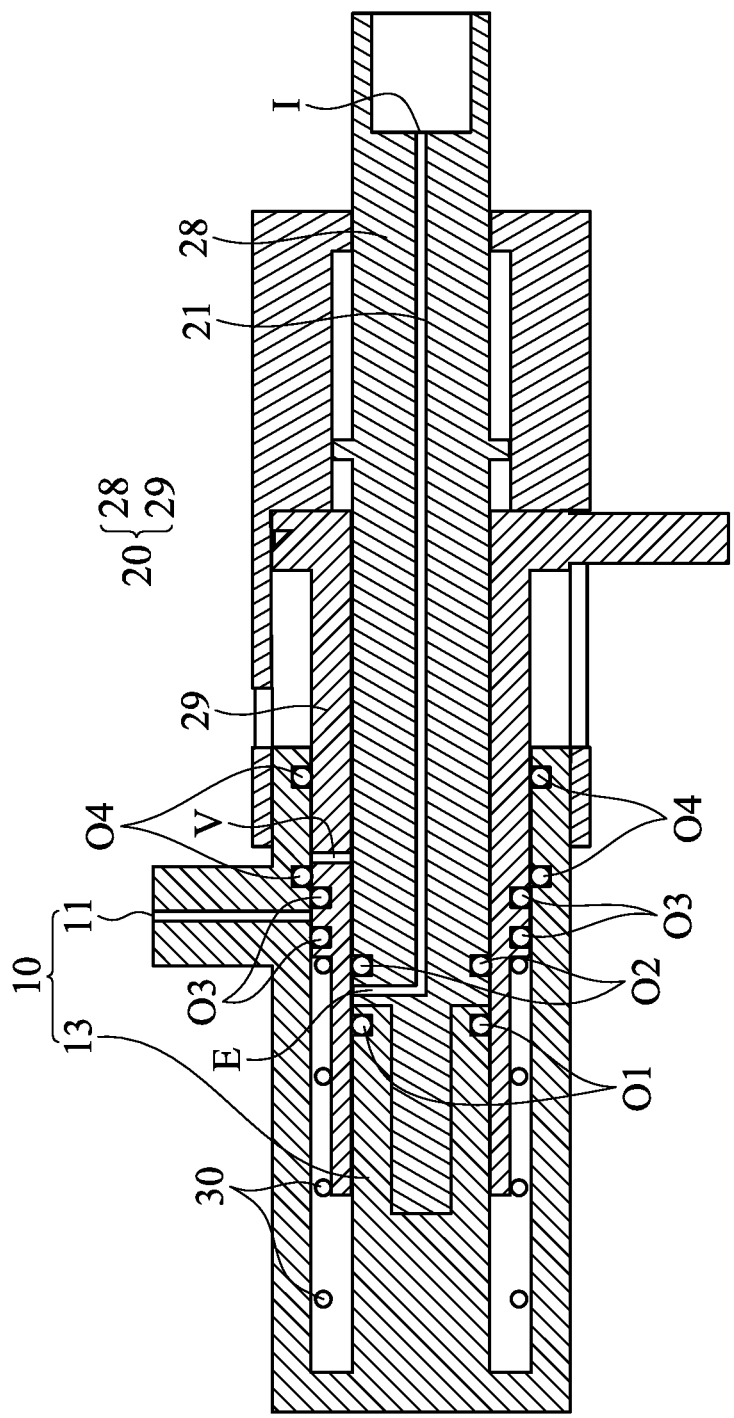
FIG. 6D is a cross-sectional view illustrating that the core tube of the gas storage unit moves to the third position relative to the discharging unit.

Referring to FIG. 6D, FIG. 6D is a cross-sectional view illustrating that the core tube 29 in FIG. 6A moves to the third position, which is shown in FIG. 5C, relative to the discharging unit 10. It is shown in FIG. 6D that when the biasing assembly 30 further drives the core tube 29 to slide from the second position to the third position relative to the discharging unit 10, one of the fourth seal rings O4 is located between the vent hole V and the discharging opening 11. Therefore, the pressurized gas in the vent hole V may be prevented from flowing towards the discharging opening 11. Meanwhile, the pressurized gas injection device 1 is still in a discharging ending state, and the pressurized gas injection device 1 may be charged again until the biasing assembly 30 is compressed again and the core tube 29 is driven to return to the first position relative to the discharging unit 10.

Figure 7:
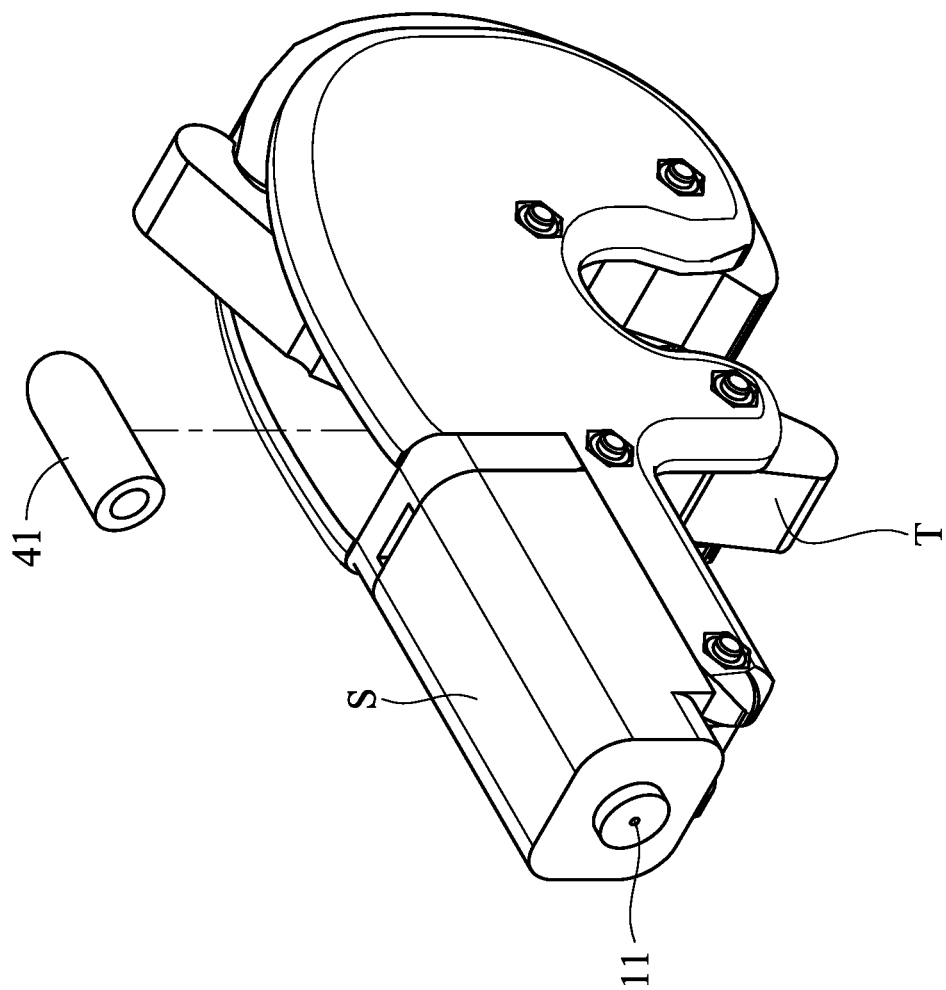
FIG. 7 is a perspective view illustrating the pressurized gas injection device in accordance with another embodiment of the present disclosure.

Then, referring to the embodiment shown in FIG. 7, the difference between the embodiments shown in FIG. 1C and FIG. 7 is that no gas injection opening G is disposed in the casing S, wherein the pressurized gas may be portably used by mounting a small gas tank (such as a bullet-shaped gas tank 41 shown in FIG. 7) in the casing S.

FIGS. 8A-8F are perspective views illustrating nozzles P in accordance with different embodiments of the present disclosure, wherein FIGS. 8C and 8D are cross-sectional views. Various types of the nozzles P shown in FIGS. 8A-8F may all be applied to any type of the aforementioned pressurized gas injection devices 1. One side of each of the nozzles P may be communicated with the discharging opening 11 of the discharging unit 10 through the one-way valve, and the other side is configured to contact skin of the patient. Therefore, the pressurized gas may be injected into the body of the patient from the discharging opening 11. As shown in FIG. 8A, in this embodiment, the nozzle P has a plurality of adjustable gas tubes such that the nozzle P may be fully attached to the surface of the skin of the patient, achieving effective contact. As shown in FIGS. 8B and 8C, a funnel-shaped structure may be formed on the inner side of the nozzle P, and is configured to evenly inject the pressurized gas to the affected part in a large area, wherein single gas tube (FIG. 8B) or a plurality of gas tubes (FIG. 8C) may be formed in the funnel-shaped structure. Moreover, as shown in FIG. 8D, the nozzle P may also have a cylindrical structure to precisely inject the pressurized gas to the affected part. Finally, as shown in FIGS. 8E and 8F, the nozzle P further includes a longitudinal flexible film or a circular patch configured to cover the affected part. Therefore, the pressurized gas may be prevented from leaking. It should be appreciated that when the gas passes through the nozzles P shown in FIGS. 8A-8F, a tremor may be generated at the place contacting the skin.

In the pressurized gas injection devices 1 of aforementioned various embodiments of the present disclosure, the gas storage unit 20 is movable relative to the discharging unit 10, and the pressurized gas may be driven to penetrate skin and reach subcutaneous tissue. Therefore, good healing effect can be achieved. On the other hand, the quantity of the auxiliary gas storage units 20' may also be properly adjusted, and the auxiliary gas storage units 20' are controlled to be located at the closed or open position. That way, pressurized gases with different volumes are selectively provided so that volume control, which is direct to the injected gas, can be performed. In addition, the pressurized gas may be selectively set to be released in a specific period by adjusting the gap between the gap adjusting component 28 and the protruding portion 13. Thus, a good control, which is the injection time and the discharging amount of the gas, may be performed. On the other hand, in the present disclosure, a disposable bullet-shaped gas tank may also be adapted as a predetermined volume for injection. The flexibility and convenience in use can be significantly enhanced by changing bullet-shaped gas tank with different volumes to adjust the required gas volume.

As set forth above, an adjustable quantitative high pressure gas injection device and method are provided in the present disclosure. The gas may be from one or more gas source, and may include at least one of hydrogen, oxygen, nitrogen, carbon dioxide, ozone, and nitrous oxide, and the gas pressure is greater than 5 MPa. The gas may directly be communicated with the gas tank in the mechanism, or an external gas source. The gas may be charged to a predetermined or volume-adjustable gas storage chamber through valves corresponding to each of the gases. Alternatively, the valve may be a valve that may adjust valve-opening time, and the gas storage chamber is not required. After released, the gas passes through a nozzle selected based on the injection depth and range, wherein a one-way valve is disposed between the nozzle and the body of the mechanism to avoid backflow and contamination. The operator may exert a proper strength to human body parts to be affected. After the gas is injected, the mechanism returns to its original state by an elastic device in the mechanism so that the mechanism is ready to be used for the next injection.

Although the present disclosure has been described in the form of some specific embodiments as above, however, those are not intended to limit the present disclosure. Those skilled in the art may make various changes and alterations to the present disclosure without departing from the spirit and scope of the present disclosure. Therefore, the scope of the present disclosure should be referred to as what is defined by the appended claims.

The invention claimed is:

1. A pressurized gas injection device, comprising:
a discharging unit having a discharging opening and a vent hole;
a gas storage unit movably disposed in the discharging unit, wherein a gas channel is formed in the gas storage unit, and a chamber is connected to the gas channel, wherein a volume of the chamber is adjustable; and
two seal rings disposed on an inner wall of the discharging unit, wherein the seal rings abut the gas storage unit;
wherein when the gas storage unit is located at a first position relative to the discharging unit, pressurized gas enters the chamber through the vent hole and the gas channel in order, and the gas channel is located between the seal rings;
wherein when the gas storage unit moves from the first position to a second position relative to the discharging unit, the gas channel moves to be located between the seal rings and the discharging opening, and the pressurized gas in the chamber is released from the pressurized gas injection device through the gas channel and the discharging opening in order, wherein the pressure of the pressurized gas is greater than or equal to 5 MPa, and the pressure of the pressurized gas remains constant as the gas storage unit is moved between the first position and the second position.

2. The pressurized gas injection device as claimed in claim 1, wherein when the gas storage unit is located at the first position relative to the discharging unit, the gas channel is located between the seal rings, and the gas channel is communicated with the vent hole.

3. The pressurized gas injection device as claimed in claim 1, wherein the gas storage unit comprises a hollow body and a rod, the rod is inserted into the body in a position-adjustable manner, and the chamber, which is configured to store the pressurized gas, is formed between the body and the rod.

4. The pressurized gas injection device as claimed in claim 1, further comprising a gas injection opening, wherein when the gas storage unit is located at the first position relative to the discharging unit, the pressurized gas enters the gas storage unit through the gas injection opening, the vent hole, and the gas channel in order.

* * * * *